(12) United States Patent
Neftel et al.

(10) Patent No.: US 7,497,840 B2
(45) Date of Patent: Mar. 3, 2009

(54) SYSTEM FOR PERFORMING FLUID ADMINISTRATION

(75) Inventors: Frederic Neftel, Lausanne (CH); Florent Junod, Nyon (CH); Didier Vecten, Lausanne (CH)

(73) Assignee: Debiotech S.A., Lausanne (CH)

( * ) Notice: Subject to any disclaimer, the term of this patent is extended or adjusted under 35 U.S.C. 154(b) by 0 days.

(21) Appl. No.: 10/565,782

(22) PCT Filed: Aug. 2, 2004

(86) PCT No.: PCT/CH2004/000481

§ 371 (c)(1), (2), (4) Date: Feb. 9, 2006

(87) PCT Pub. No.: WO2005/009512

PCT Pub. Date: Feb. 3, 2005

(65) Prior Publication Data

US 2006/0189923 A1 Aug. 24, 2006

(30) Foreign Application Priority Data

Jul. 31, 2003 (WO) .................... PCT/CH03/00528

(51) Int. Cl.
*A61M 1/00* (2006.01)
(52) U.S. Cl. .............. 604/29; 604/21; 604/19
(58) Field of Classification Search ............ 604/151, 604/39, 40, 19, 21, 28, 29; 417/477.1, 474–476, 417/247, 346
See application file for complete search history.

(56) References Cited

U.S. PATENT DOCUMENTS

| | | | | |
|---|---|---|---|---|
| 4,980,054 A | * | 12/1990 | Lavender | 210/90 |
| 5,078,362 A | * | 1/1992 | Lawless et al. | 251/9 |
| 5,437,629 A | * | 8/1995 | Goldrath | 604/21 |
| 5,478,211 A | * | 12/1995 | Dominiak et al. | 417/234 |
| 6,074,359 A | * | 6/2000 | Keshaviah et al. | 604/29 |

FOREIGN PATENT DOCUMENTS

| | | |
|---|---|---|
| DE | 198 14 695 | 10/1999 |
| DE | 1 195 171 | 4/2002 |
| DE | 101 24 951 | 12/2002 |

* cited by examiner

*Primary Examiner*—Nicholas D Lucchesi
*Assistant Examiner*—Laura A Bouchelle
(74) *Attorney, Agent, or Firm*—Nixon & Vanderhye P.C.

(57) ABSTRACT

The invention concerns a system and a method of use of said system for performing fluid administration on a patient, the system comprising:
  a liquid pump (1),
  a liquid distribution system (2) connected to said pump (1) in such a way that liquid can flow from the liquid distribution system (2) to the pump (1) and vice versa,
  liquid supply means (3) for supplying liquid to a patient (4) via said liquid distribution system (2) and said pump (1),
  a patient conduit (5) adapted for connecting said liquid distribution system (2) to a patient (4),
the system being characterized by the fact that said liquid pump (1) is unidirectional and that said liquid distribution system (2) comprises switching means designed to alternatively connect the pump enter line (56) with the supply means (3) or with the patient conduit (5).

21 Claims, 29 Drawing Sheets

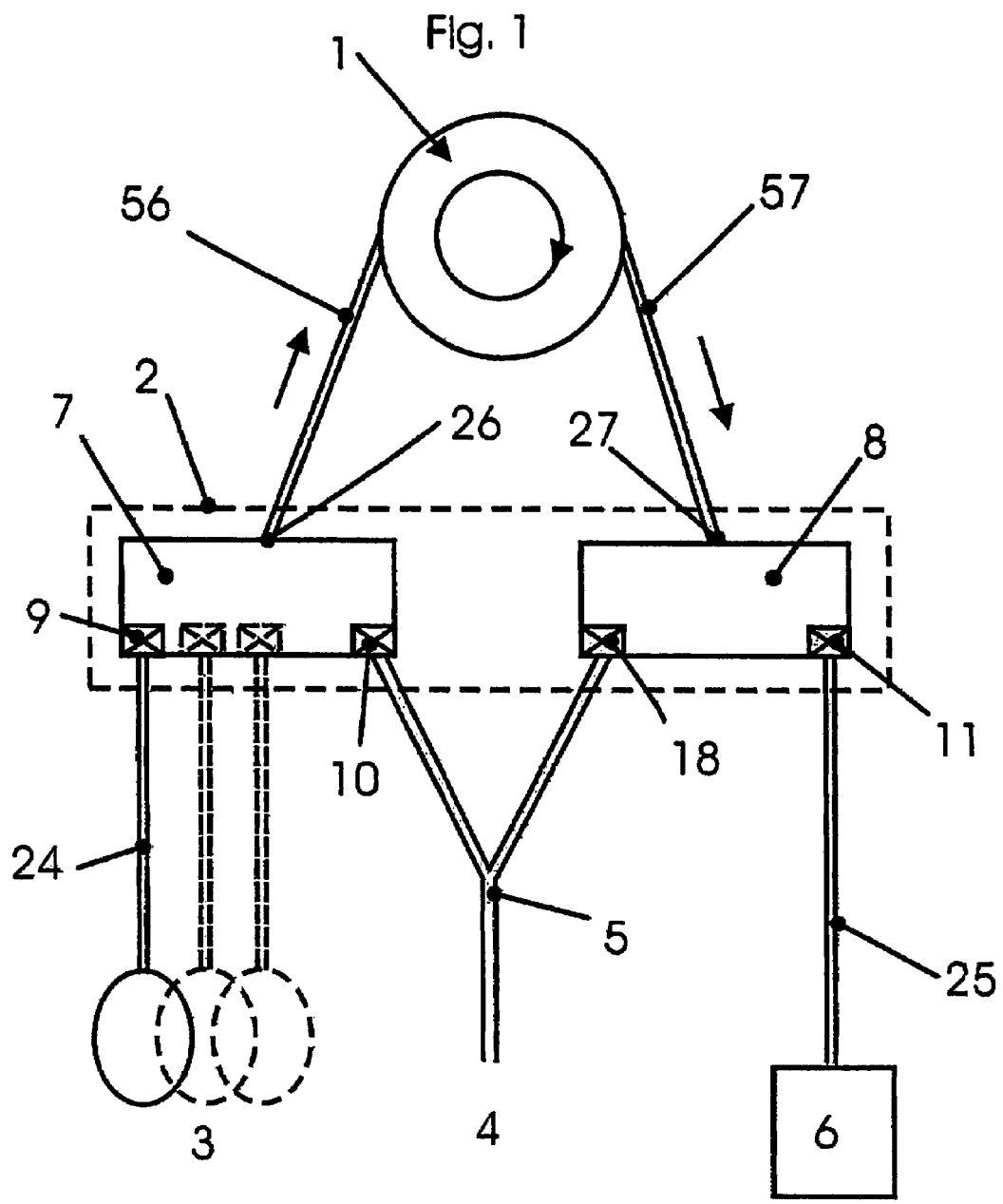

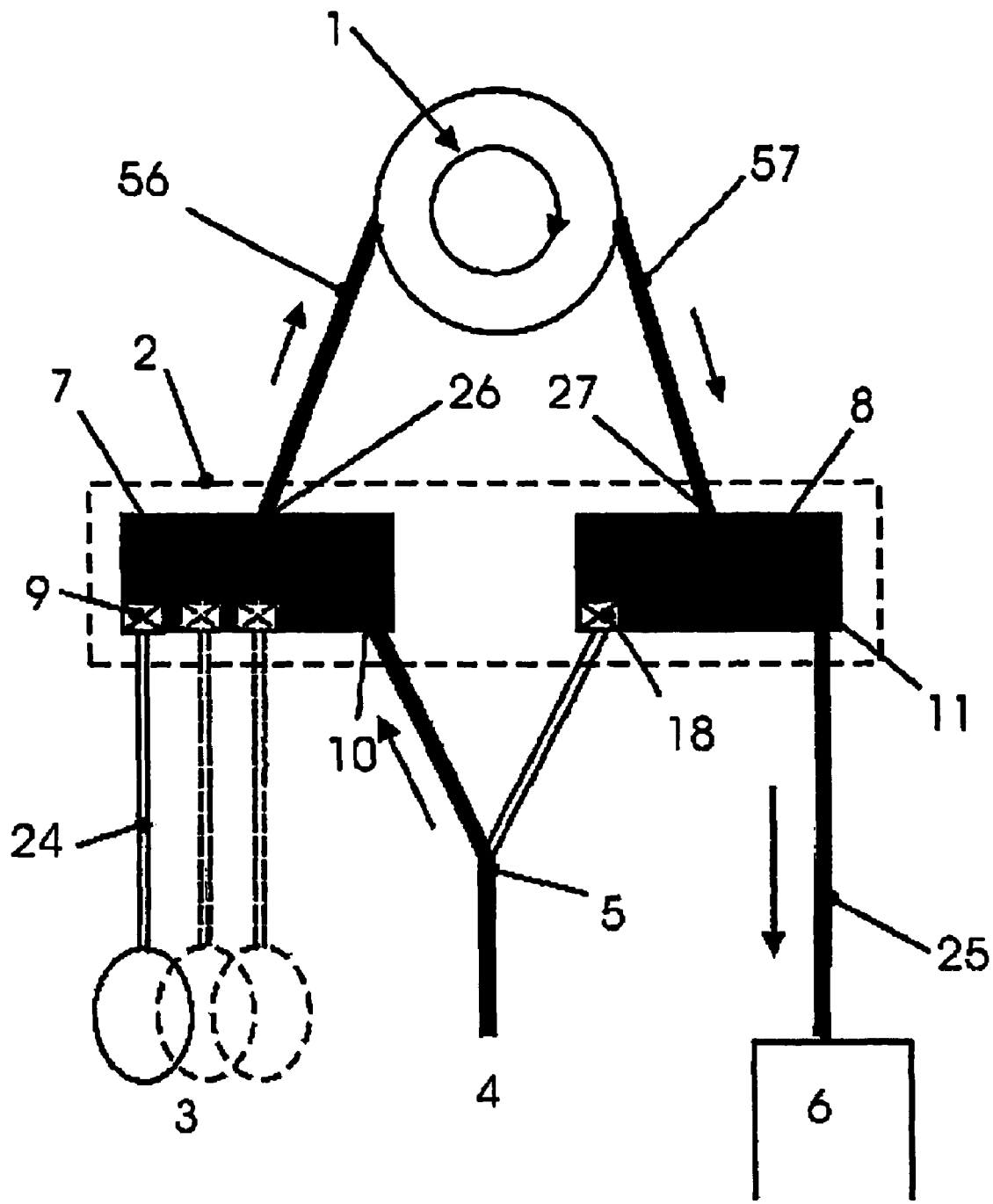

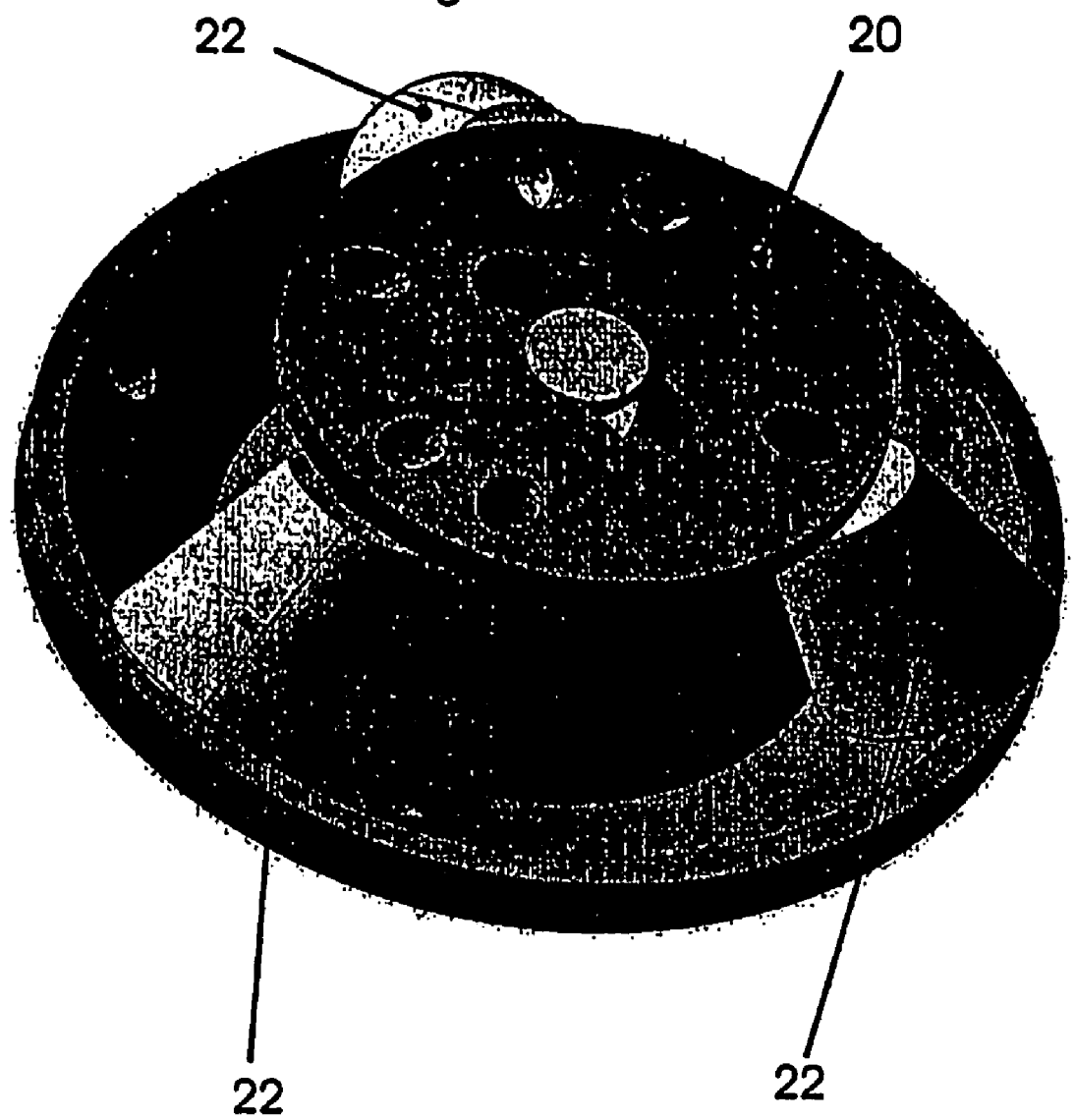

FIG. 25

DRAIN ANALISYS APD

Figure 1A:
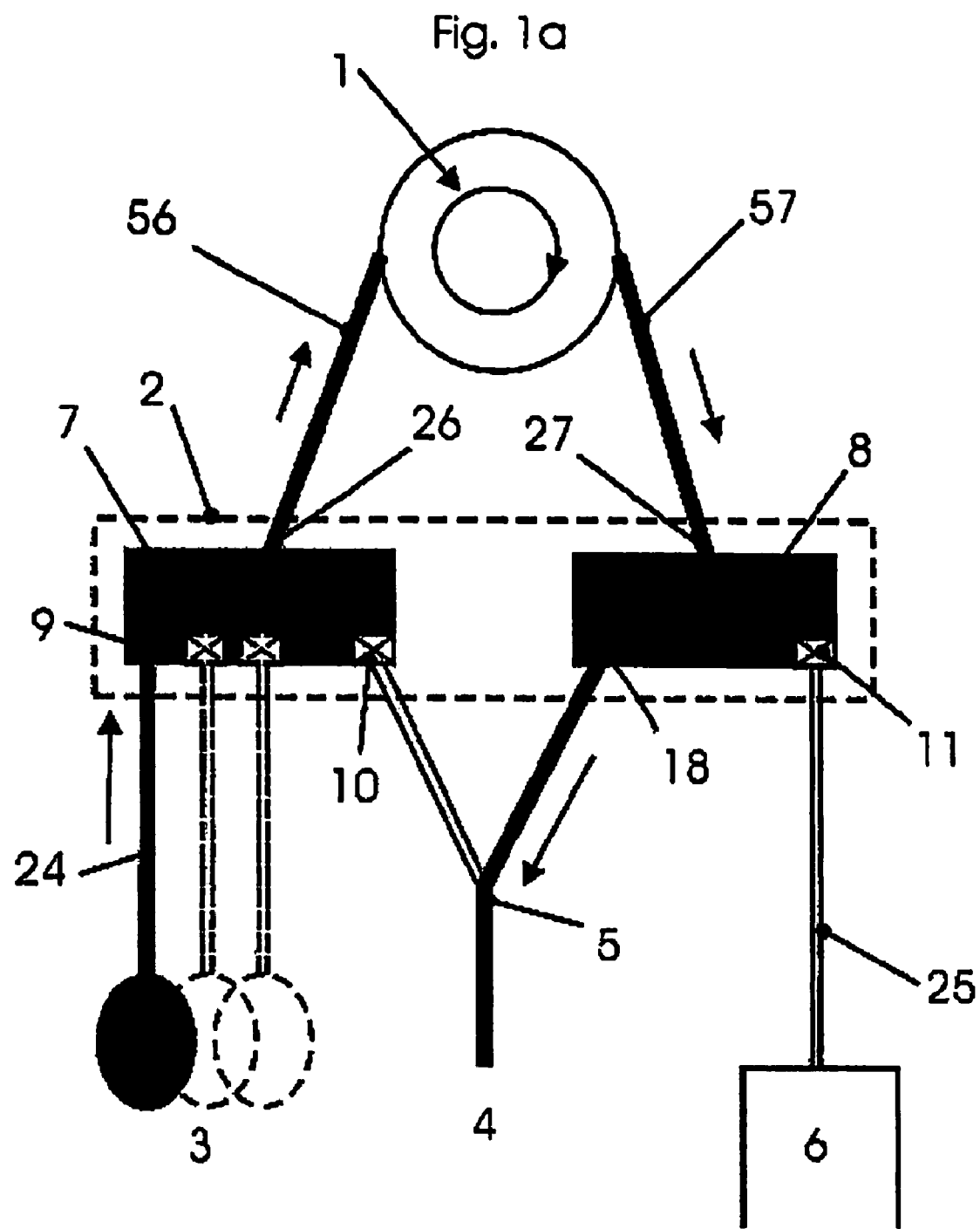

| [min] | Cycle 1 Vol. [ml] | Cycle 1 Q [l/[min] | | Cycle 2 Vol. [ml] | Cycle 2 Q [l/[min] | | Cycle 3 Vol. [ml] | Cycle 3 Q [l/[min] | | Cycle 4 Vol. [ml] | Cycle 4 Q [l/[min] | | Cycle 5 Vol. [ml] | Cycle 5 Q [l/[min] |
|---|---|---|---|---|---|---|---|---|---|---|---|---|---|---|
| 0 | 2330 | | | 2752 | | | 2503 | | | 2665 | | | 2736 | |
| 1 | 2131 | 0.199 | | 2600 | 0.152 | | 2294 | 0.209 | | 2490 | 0.175 | | 2580 | 0.156 |
| 2 | 1900 | 0.234 | | 2375 | 0.225 | | 2087 | 0.207 | | 2253 | 0.237 | | 2348 | 0.232 |
| 3 | 1681 | 0.219 | | 2158 | 0.217 | | 1860 | 0.227 | | 2035 | 0.218 | | 2120 | 0.228 |
| 4 | 1453 | 0.228 | | 1941 | 0.217 | | 1637 | 0.223 | | 1809 | 0.226 | | 1892 | 0.228 |
| 5 | 1233 | 0.220 | | 1725 | 0.216 | | 1420 | 0.217 | | 1585 | 0.224 | | 1651 | 0.241 |
| 6 | 1023 | 0.210 | | 1499 | 0.226 | | 1193 | 0.227 | | 1369 | 0.216 | | 1421 | 0.230 |
| 7 | 797 | 0.226 | | 1292 | 0.207 | | 976 | 0.217 | | 1143 | 0.226 | | 1200 | 0.221 |
| 8 | 579 | 0.218 | | 1075 | 0.217 | | 750 | 0.226 | | 927 | 0.216 | | 991 | 0.209 |
| 9 | 367 | 0.212 | | 848 | 0.227 | | 532 | 0.218 | | 721 | 0.206 | | 784 | 0.207 |
| 10 | 173 | 0.194 | | 644 | 0.204 | | 326 | 0.206 | treshold 1 | 512 | 0.209 | | 583 | 0.201 |
| 11 | 72 | 0.101 | treshold 1 | 437 | 0.207 | | 147 | 0.179 | treshold 2 | 433 | 0.079 | treshold 1 | 404 | 0.179 | treshold 1 |
| 12 | | | treshold 2 | 232 | 0.205 | | 72 | 0.075 | Q [l/[min] | 374 | 0.059 | | 302 | 0.102 |
| 13 | | | Q [l/[min] | 74 | 0.158 | treshold 1 | | | 0.2142 | 307 | 0.067 | treshold 2 | 228 | 0.074 | treshold 2 |
| 14 | | | 0.216 | | | treshold 2 | | | 0.075 | | 0.094 | Q [l/[min] | | | Q [l/[min] |
| 15 | | | 0.101 | | | Q [l/[min] | | | 0.024 | | | 0.2153 | | | 0.212 |
| 16 | | | 0.017 | | | 0.21 | | | | | | | | | |
| 17 | | | | | | 0.158 | | | | | | | | | 0.088 |
| 18 | | | | | | 0.0185 | | | | | | | | | 0.021 |
| 19 | | | | | | | | | | | | | | | |
| 20 | | | | | | | | | | | | 0.075 | | | |
| 21 | | | | | | | | | | | | 0.030 | | | |
| 22 | | | | | | | | | | | | | | | |
| 23 | | | | | | | | | | | | | | | |
| 24 | | | | | | | | | | | | | | | |

Patient BH

SYSTEM FOR PERFORMING FLUID ADMINISTRATION

This application is the U.S. national phase of international application PCT/CH2004/000481 filed 2 Aug. 2004 which designated the U.S. and claims benefit of PCT/CH03/00528, dated 31 Jul. 2003, the entire content of which is hereby incorporated by reference.

FIELD OF THE INVENTION

The present invention relates to systems for performing peritoneal dialysis on a patient and more precisely to such systems which include a pump.

STATE OF THE ART

Peritoneal dialysis systems as defined above are described in the following patent documents: EP 0 790 841 B1, EP 0 695 397 B1, EP 0 852 953 B1, EP 0 694 125 B1, EP 0 686 237 B1, EP 0 471 000 B1, EP 0 332 690 B1, EP 0 262 182 B1, EP 0 259 464 B1 and EP 1 195 171 A2.

SUMMARY OF THE INVENTION

An objective of the present invention is to provide an improved peritoneal dialysis system and in particular an improved liquid distribution system.

This objective and many others are achieved with the system as defined in the claims.

Preferred embodiments of the invention are defined in dependent claims.

Several advantages result from the invention, in particular:
- simpler, and therefore more efficient, liquid distribution system which may include only two distinct cavities,
- possibility to use a peristaltic pump, in particular a rotatable peristaltic pump,
- possibility to use an unidirectional pump which results in a higher precision and a longer life time,
- possibility to fix the liquid distribution system and the pump together, alternatively with vibration attenuating means,
- possibility to use a flexible membrane which covers the chambers and which include valve elements,
- the membrane may be molded,
- part of a pressure sensor can be incorporated in the membrane.

Those and other advantages will be better understood in the detailed description of the invention exemplified here below, together with the following figures.

SHORT DESCRIPTION OF THE FIGURES

Figure 2:
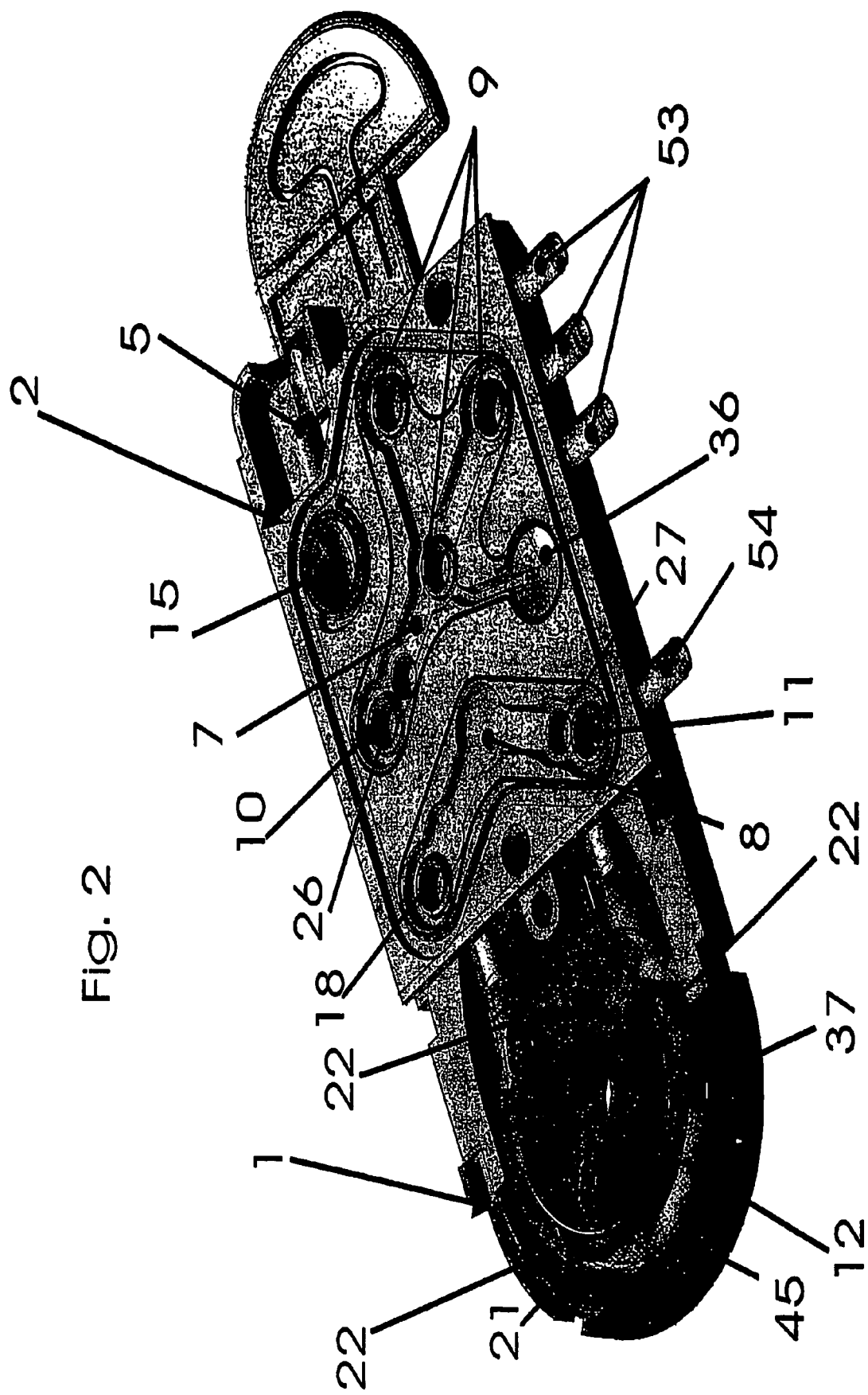
Figure 3:
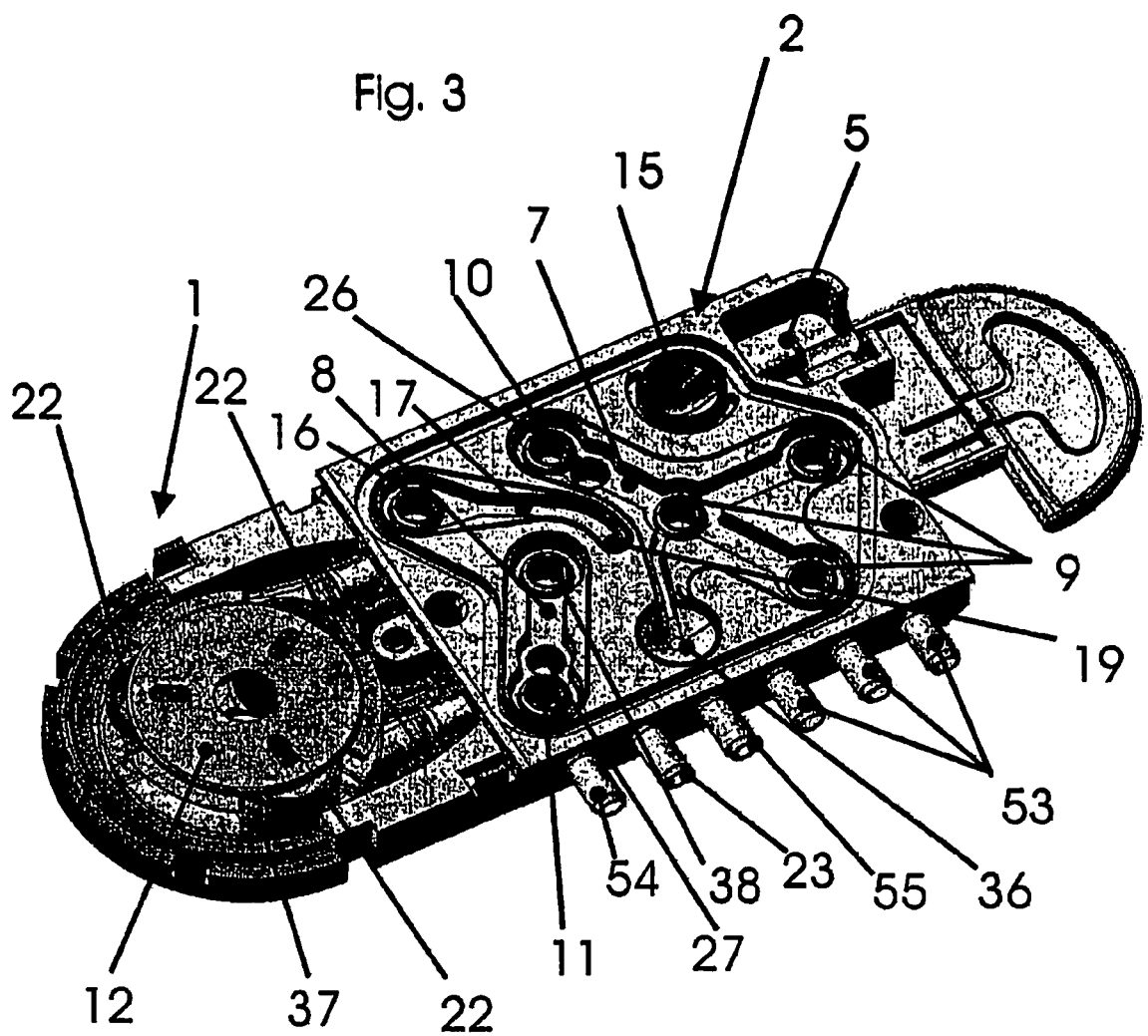
Figure 4:
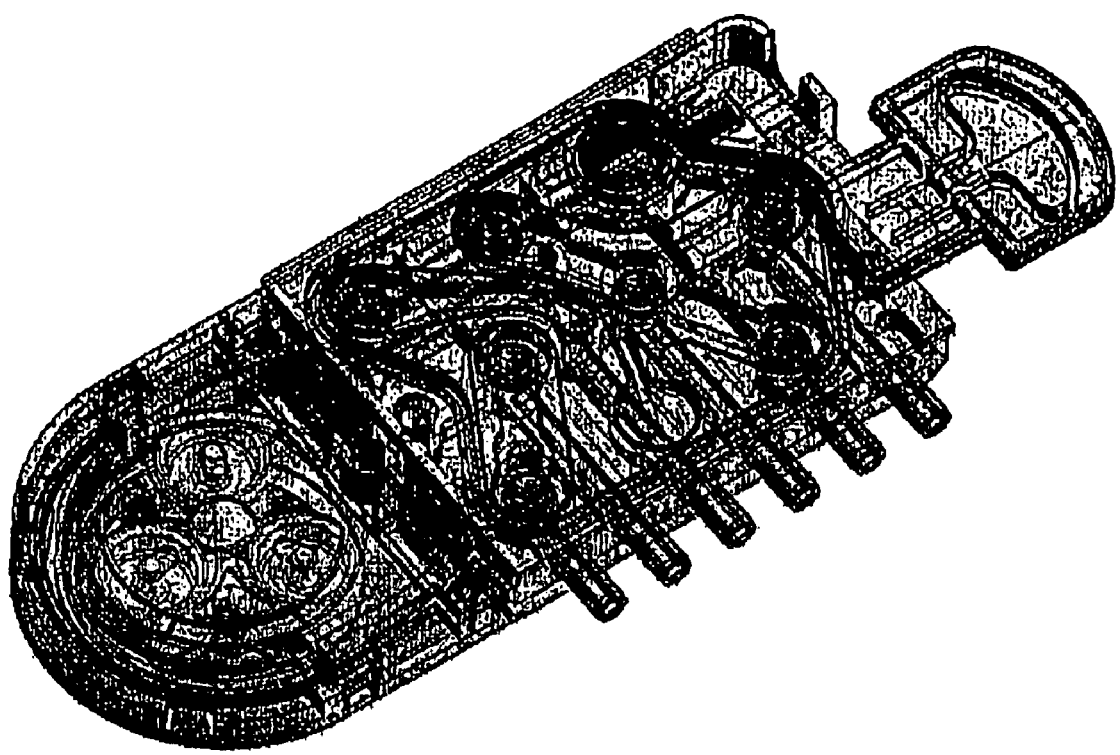
Figure 5:
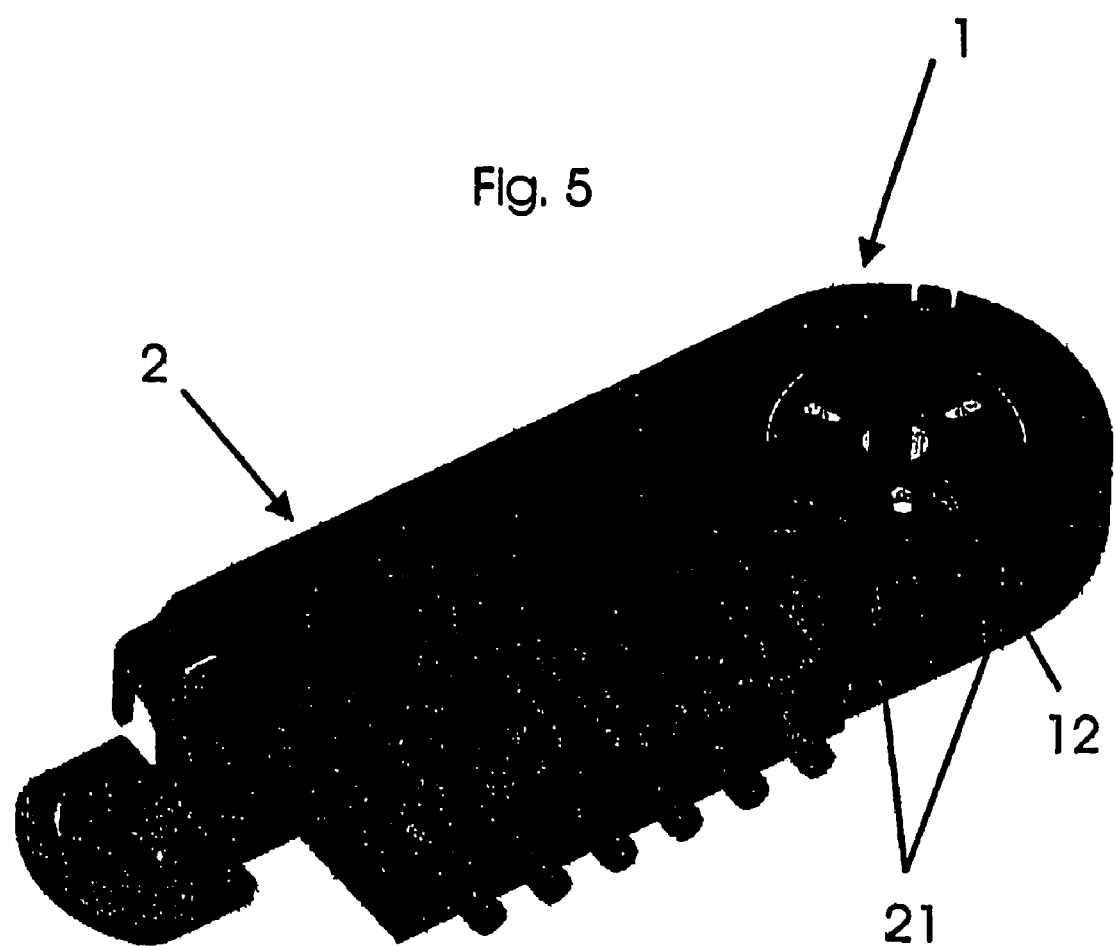
Figure 6:
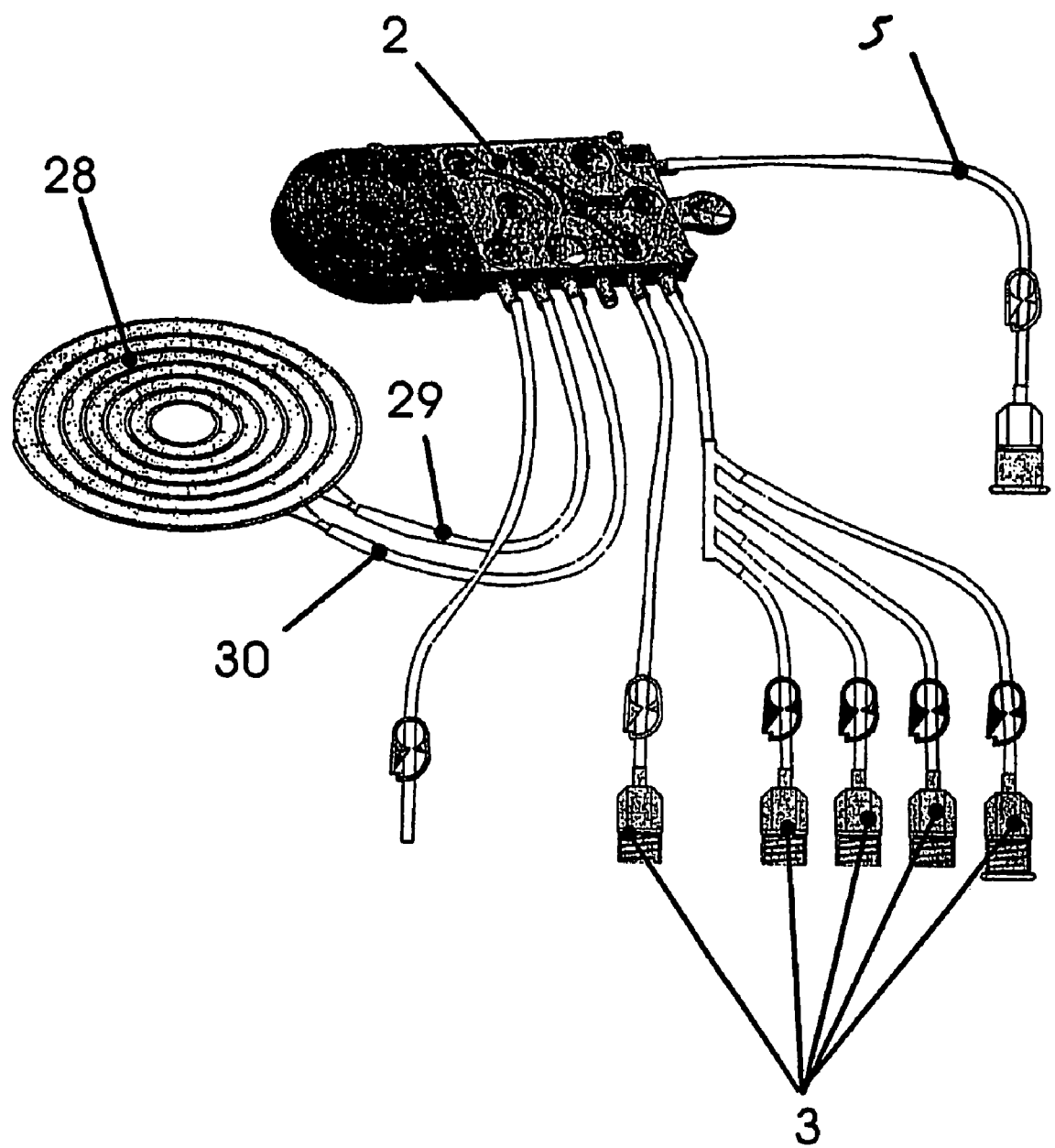
Figure 7:
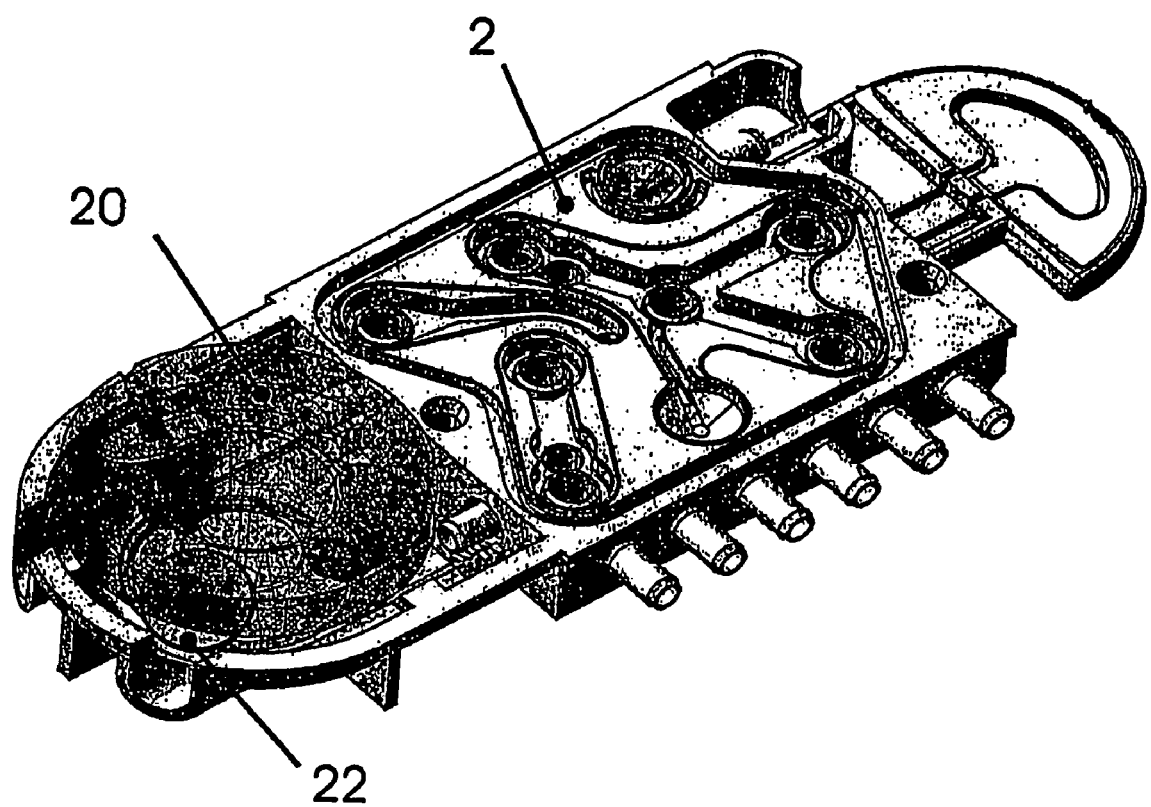
Figure 8:
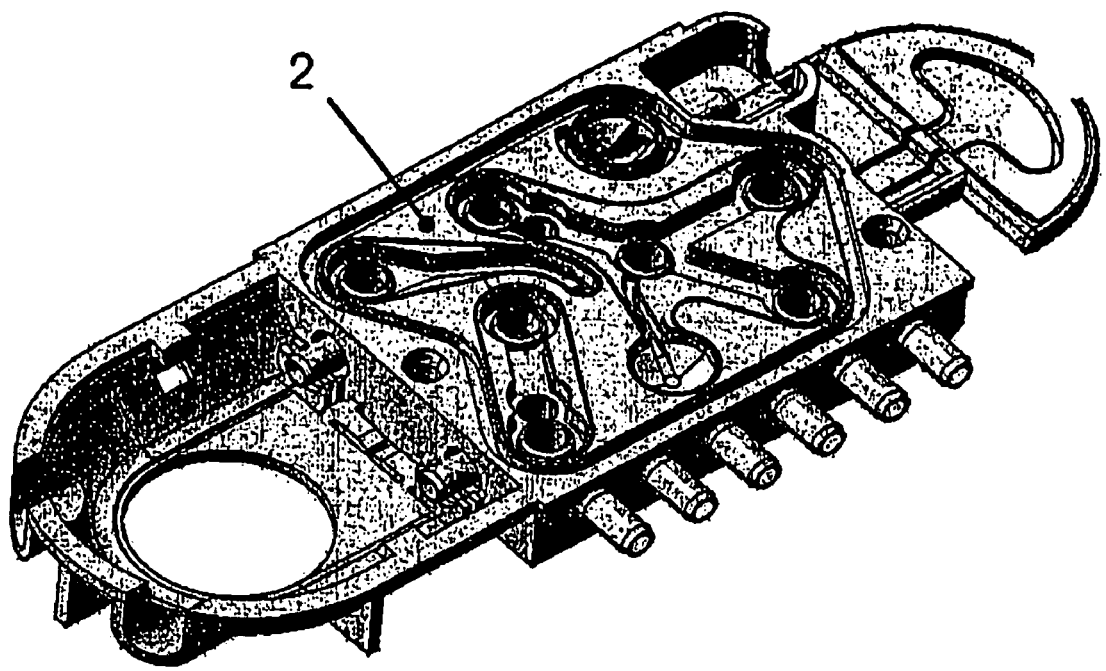
Figure 9:
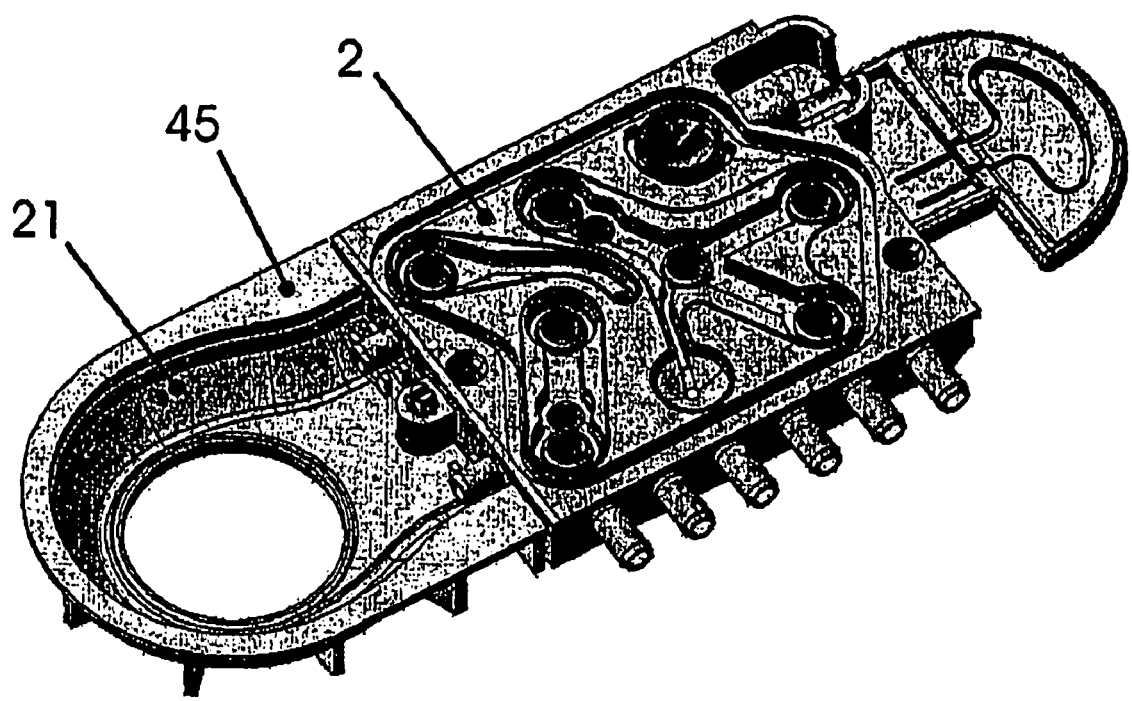
Figure 10:
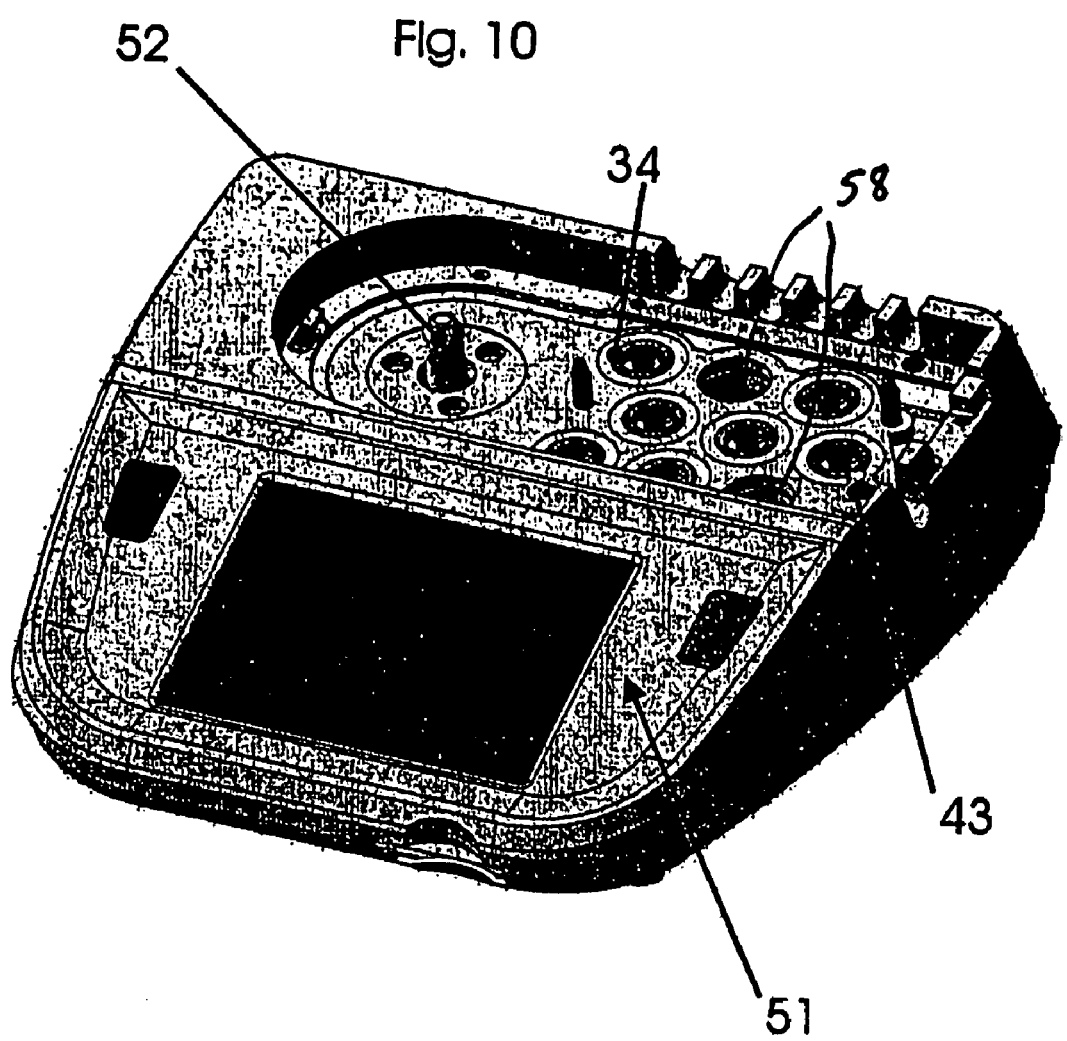
Figure 11:
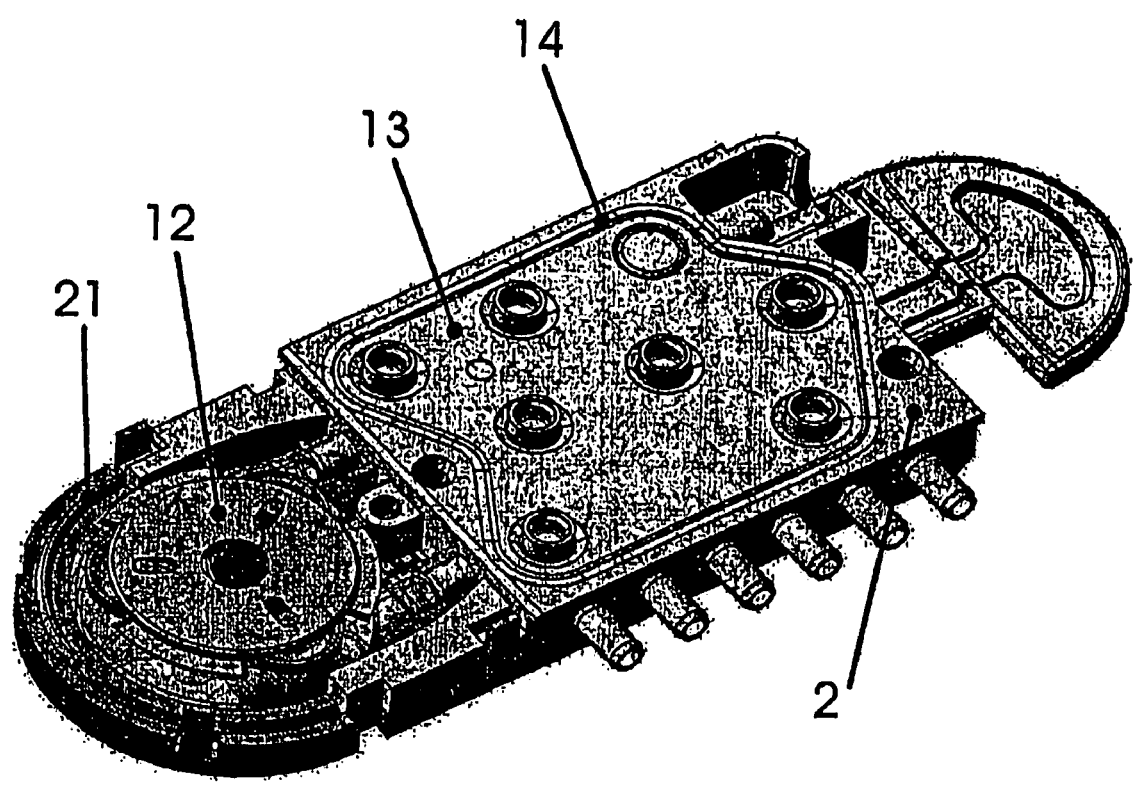
Figure 12:
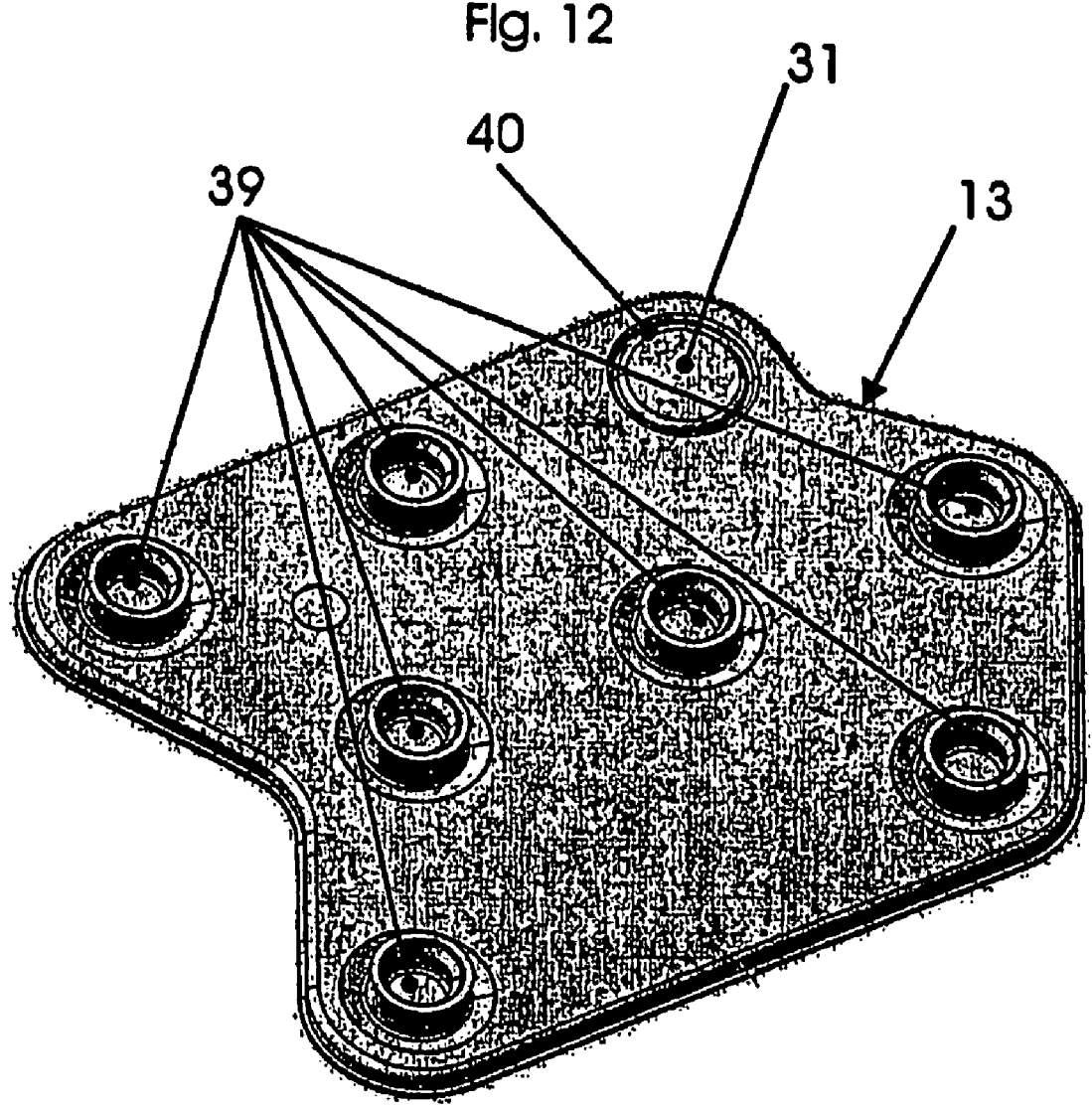
Figure 13:
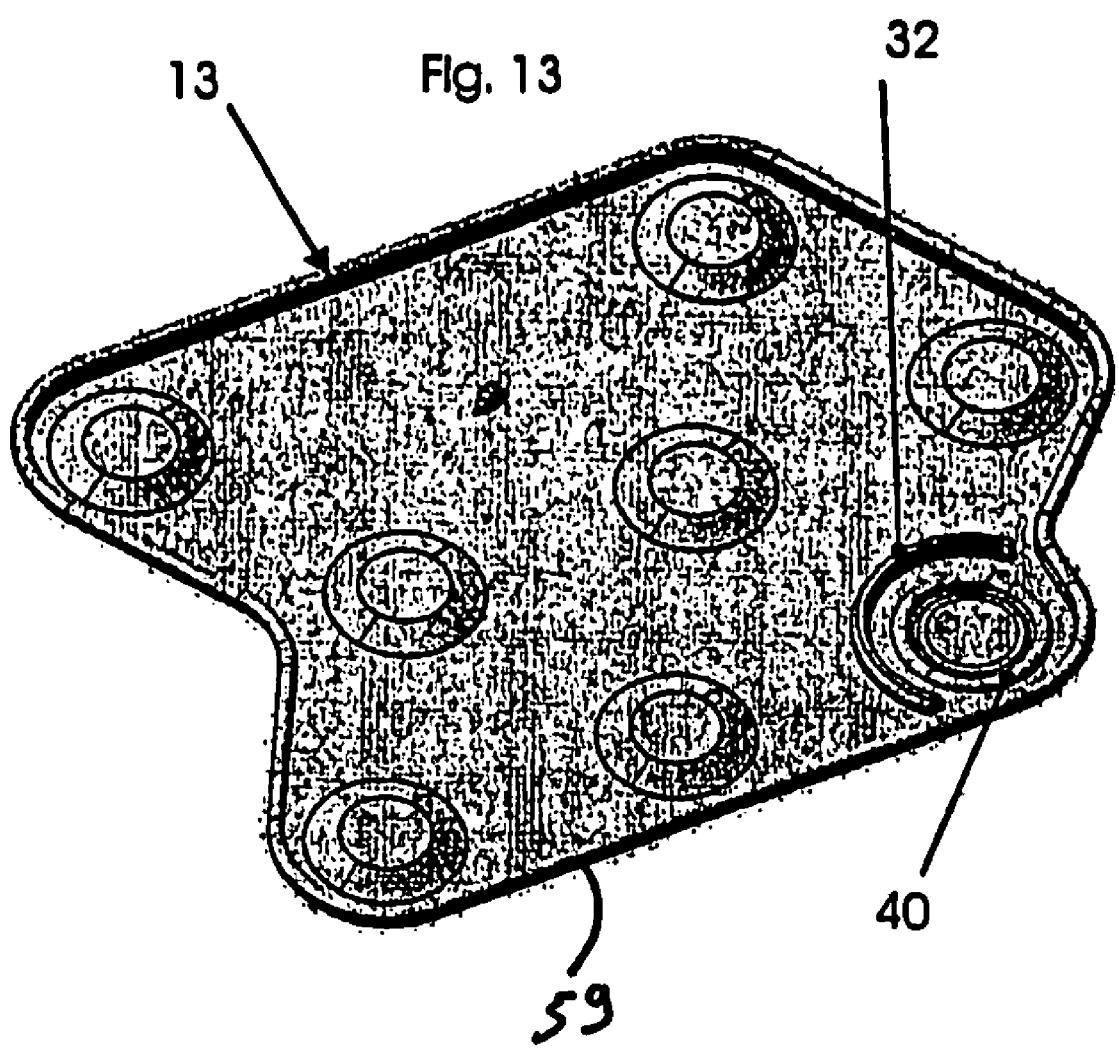
Figure 14:
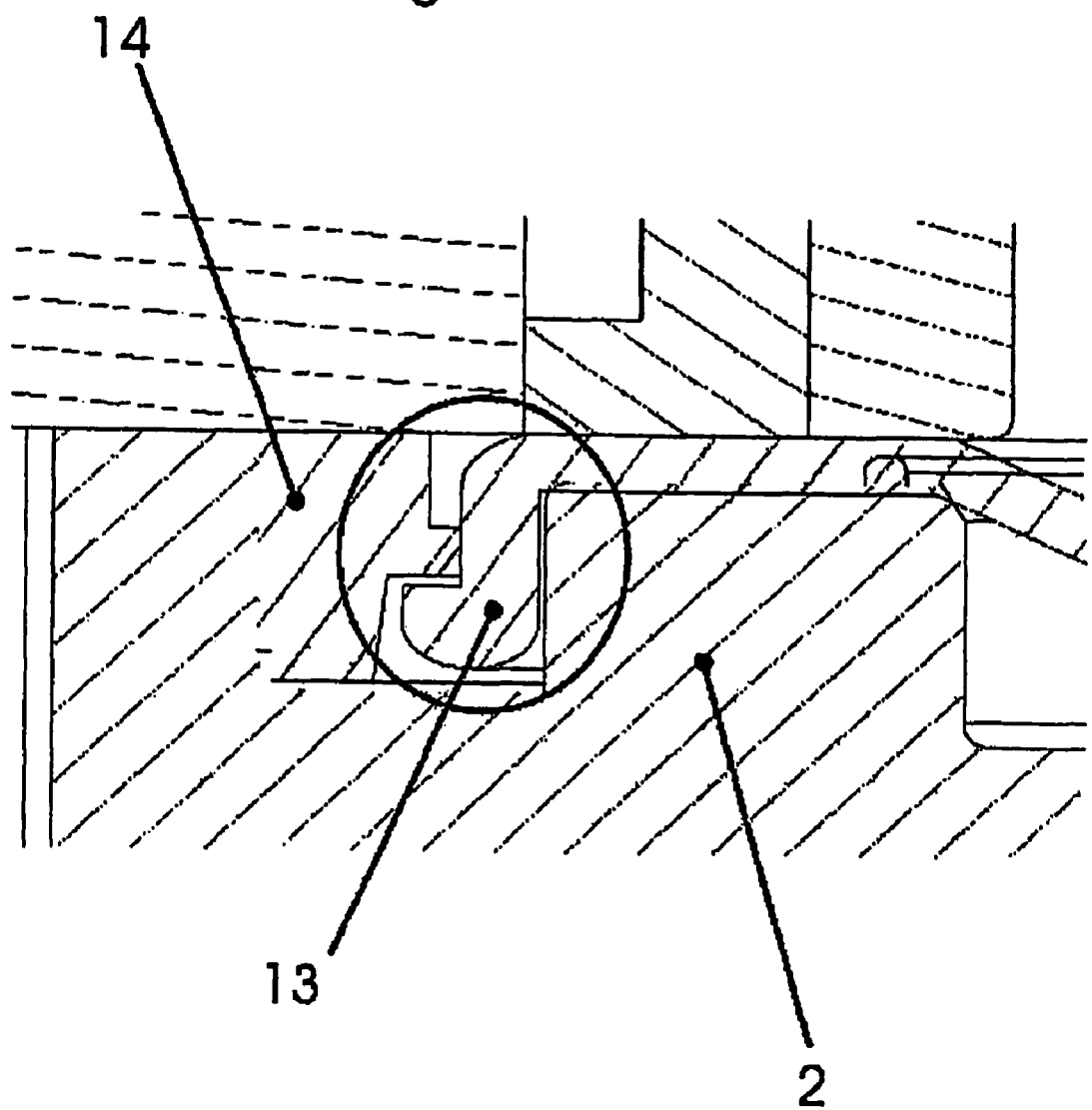
Figure 14A:
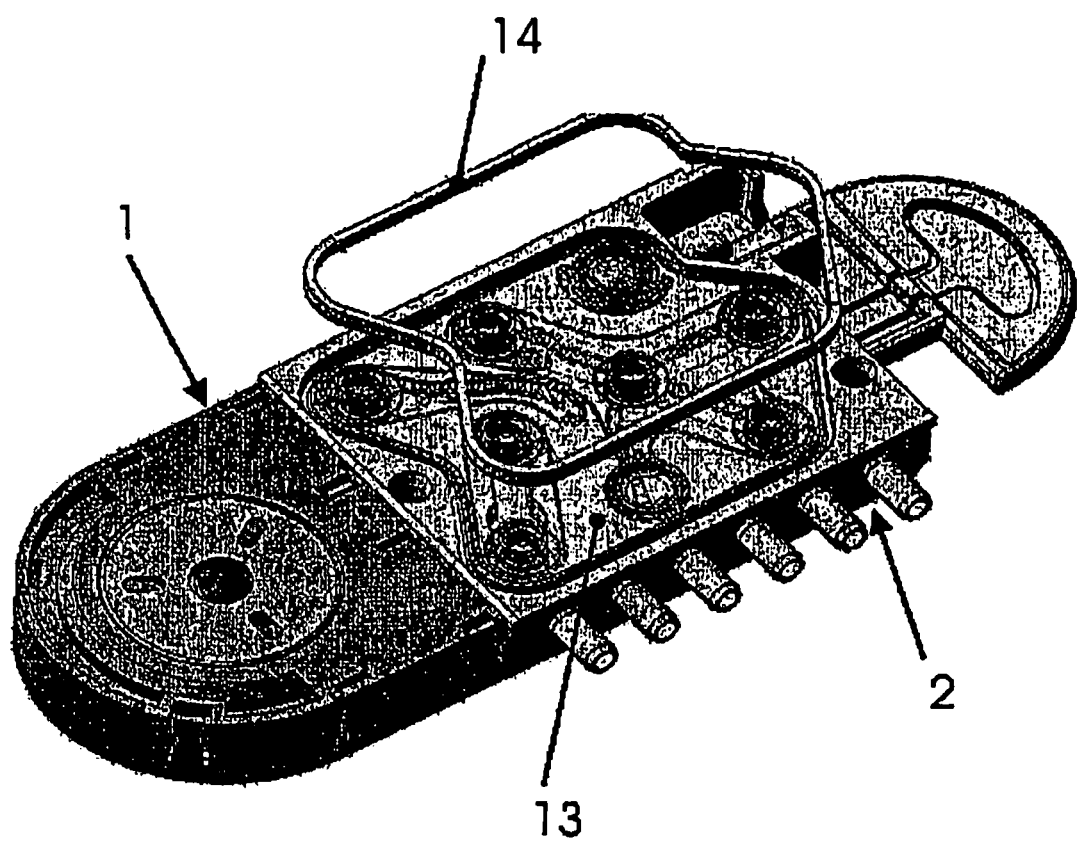
Figure 15:
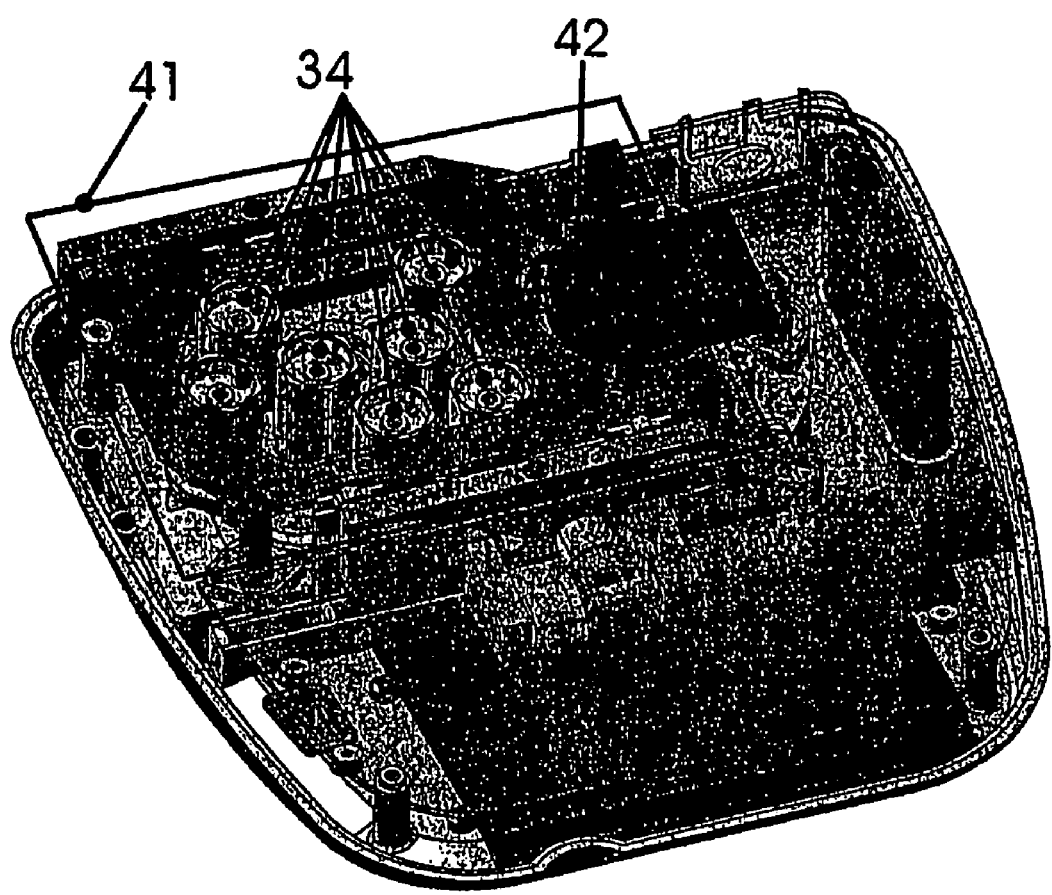
Figure 16:
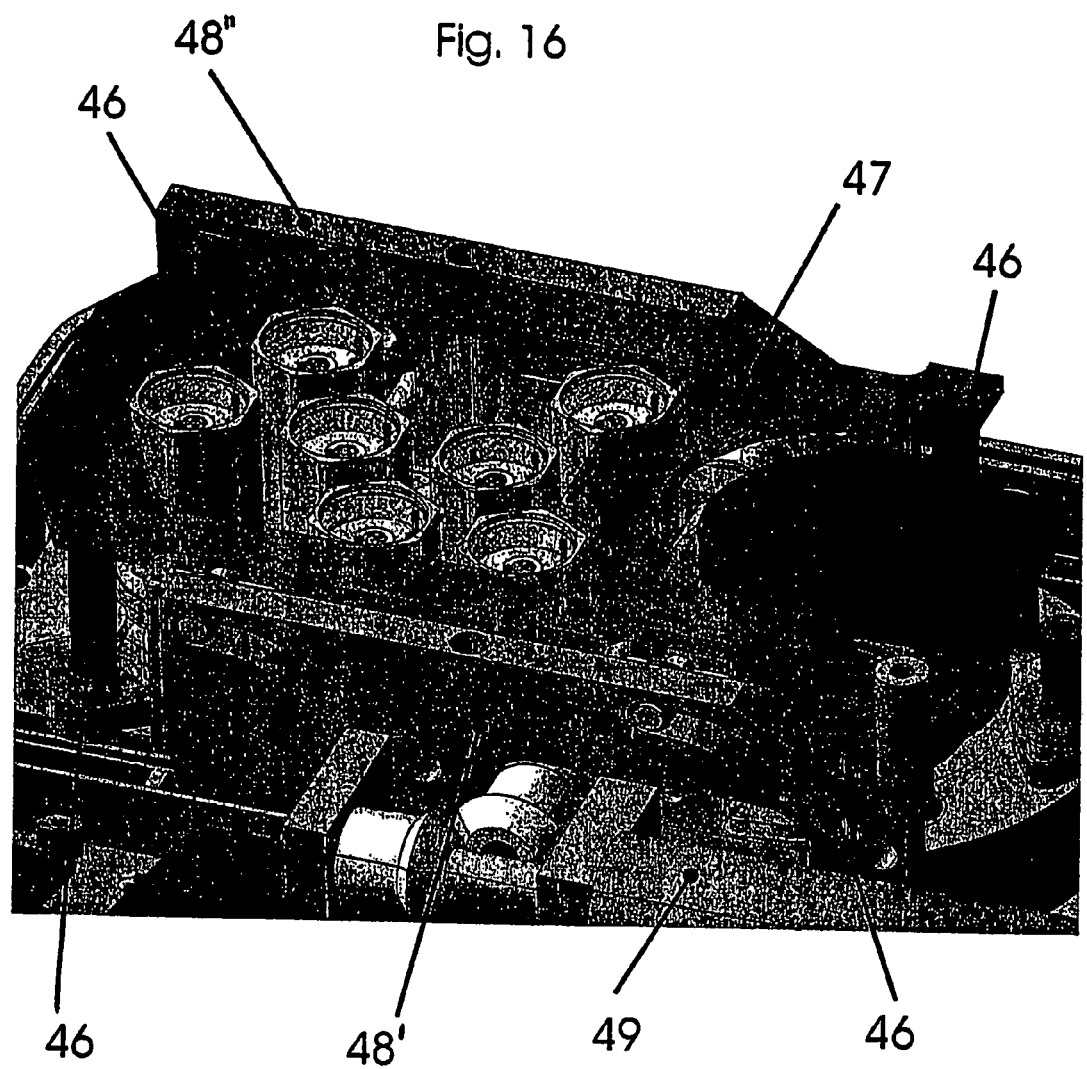
Figure 17:
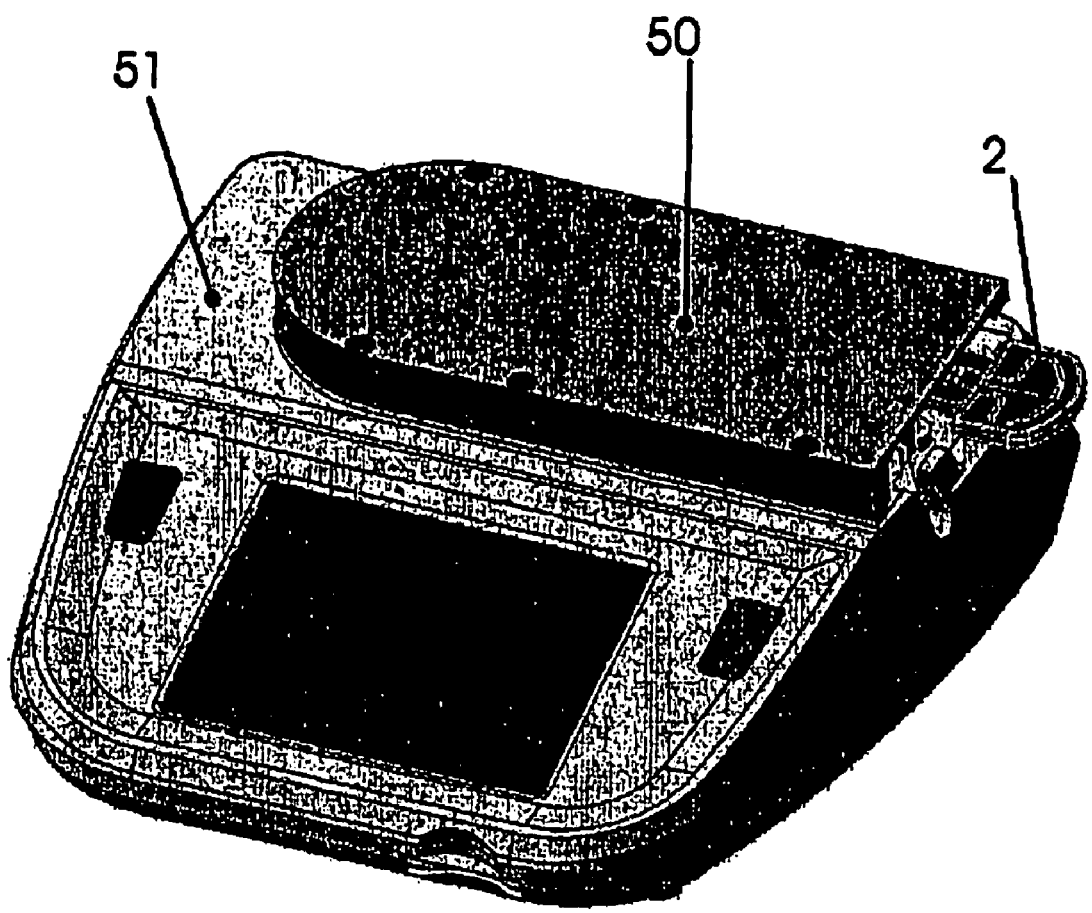
Figure 18:
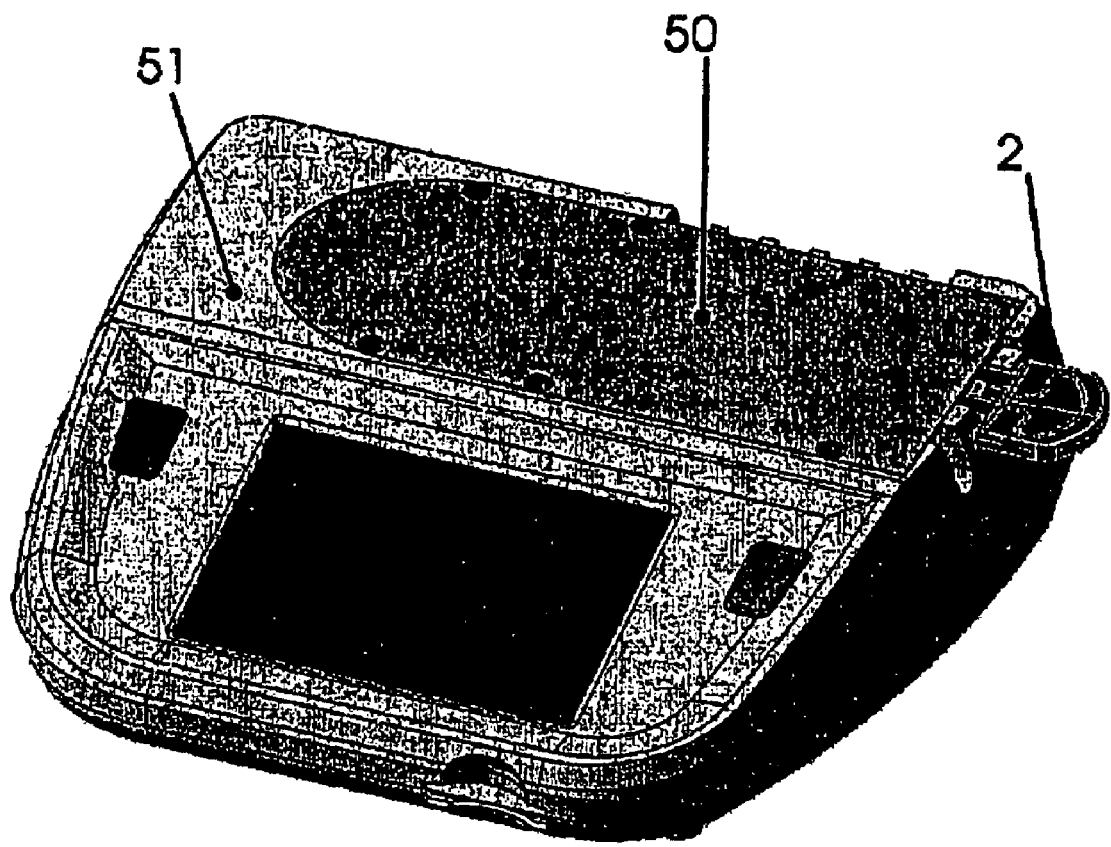
Figure 19:
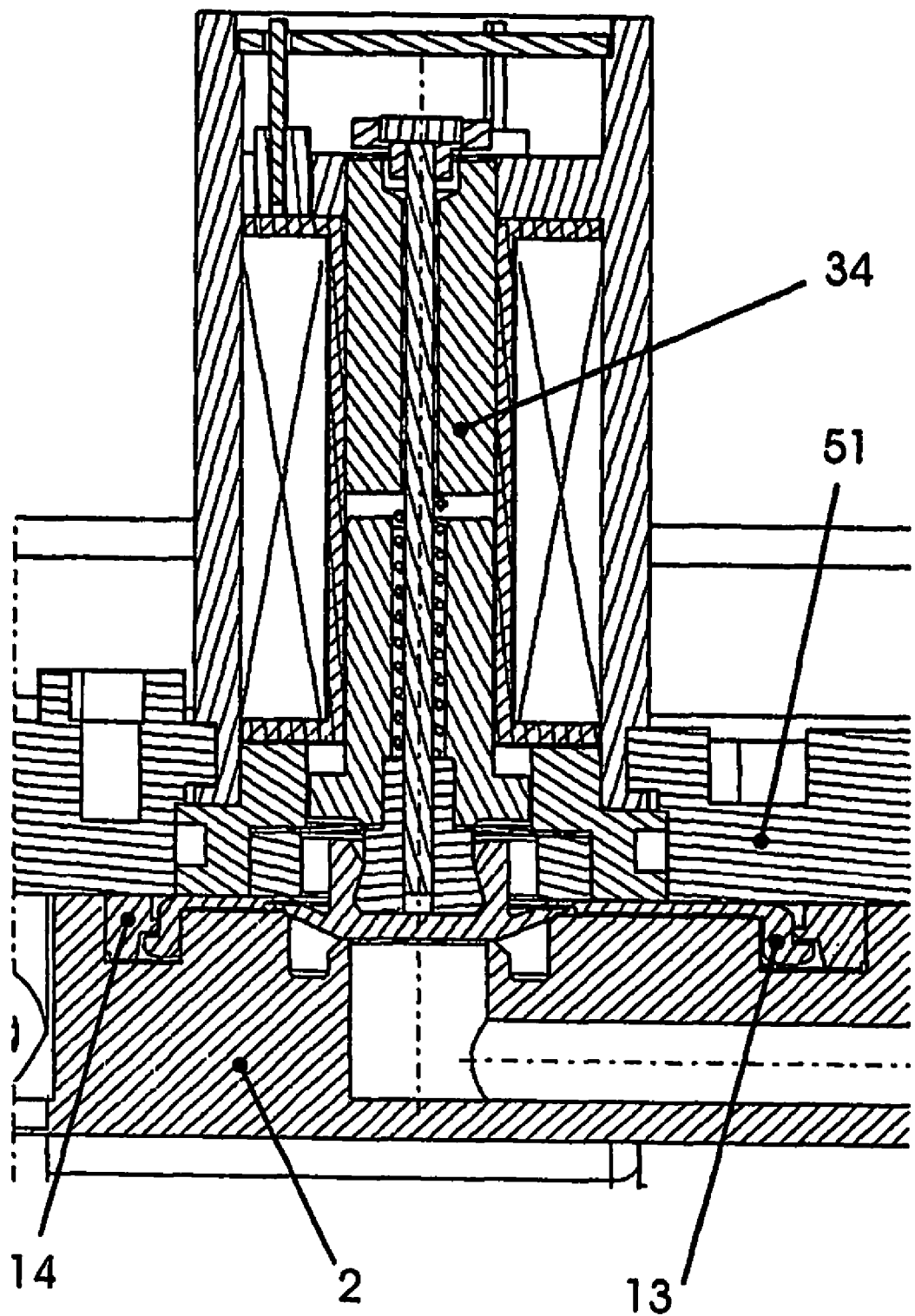
Figure 20:
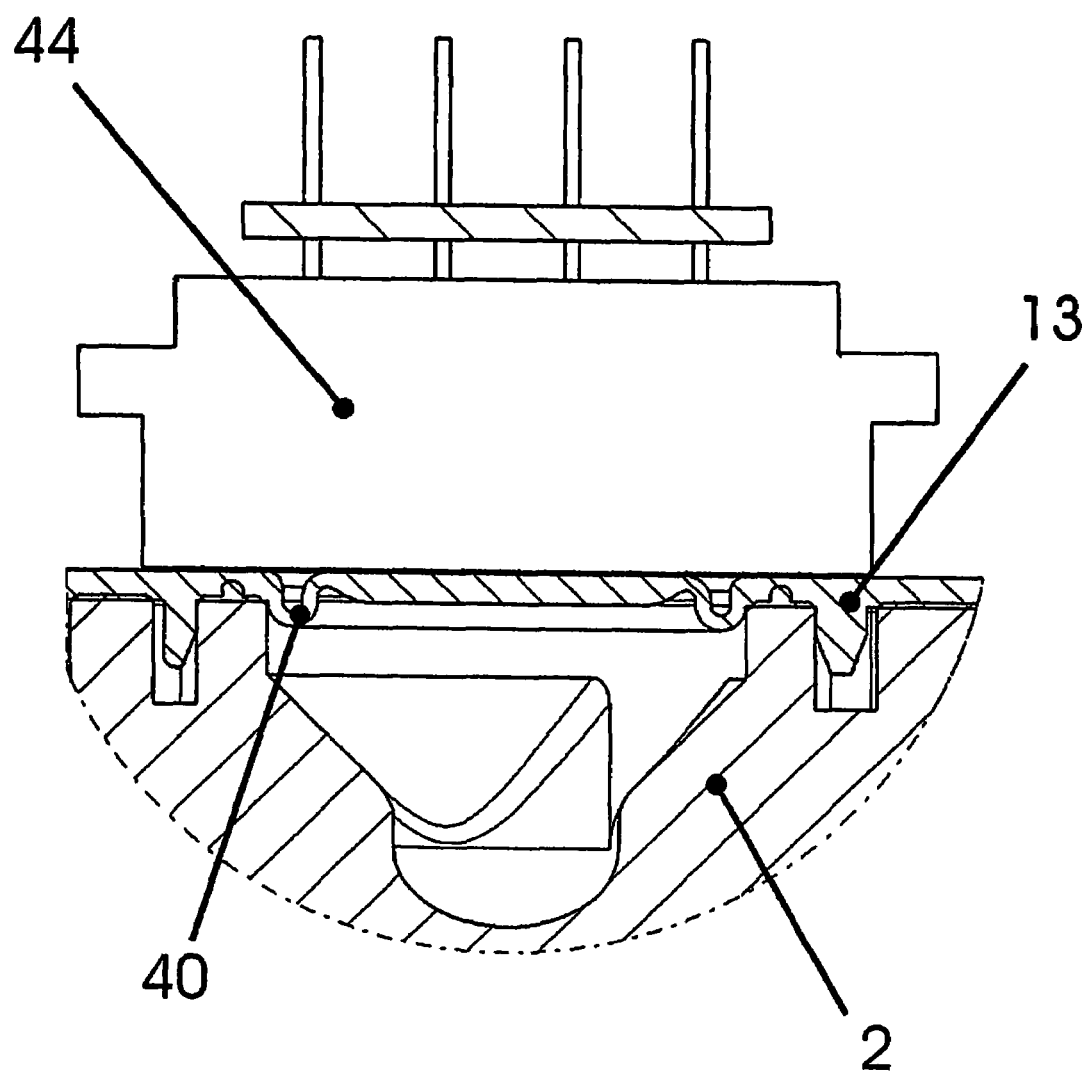
Figure 21:
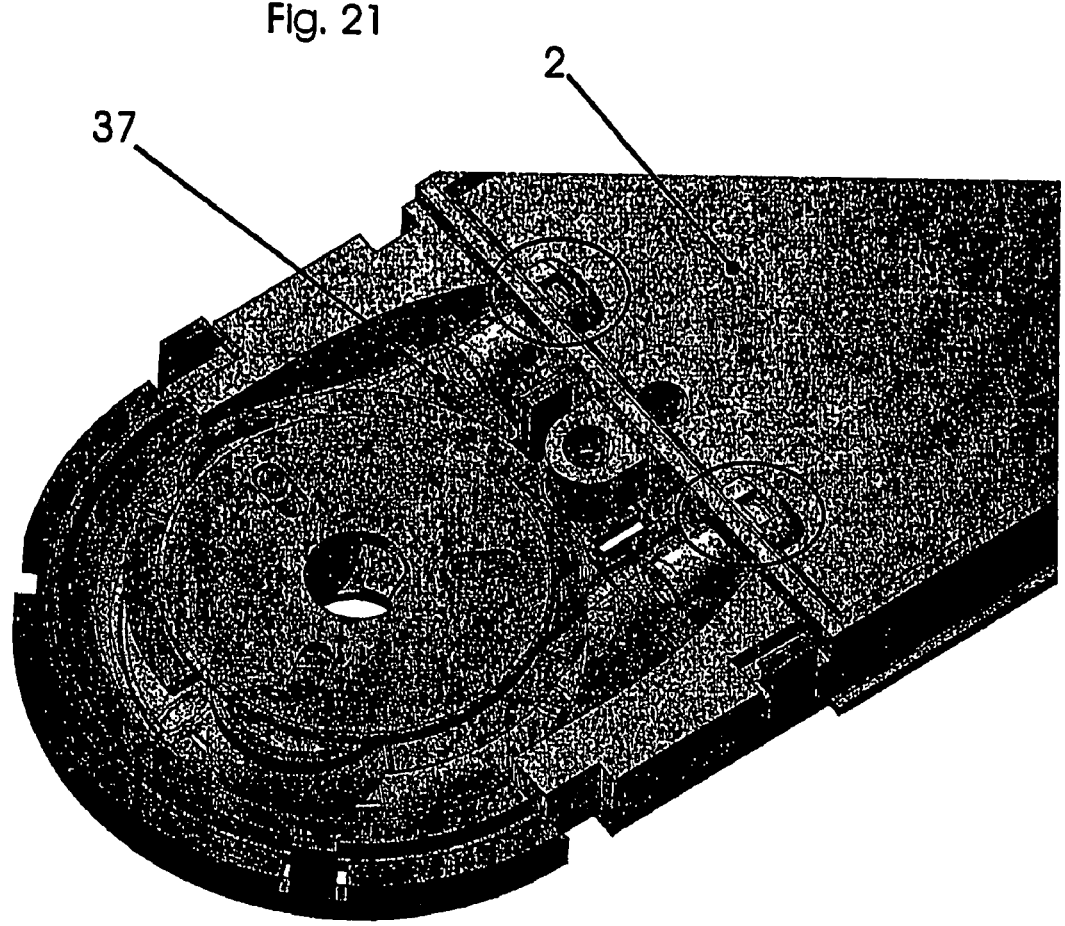
Figure 22A:
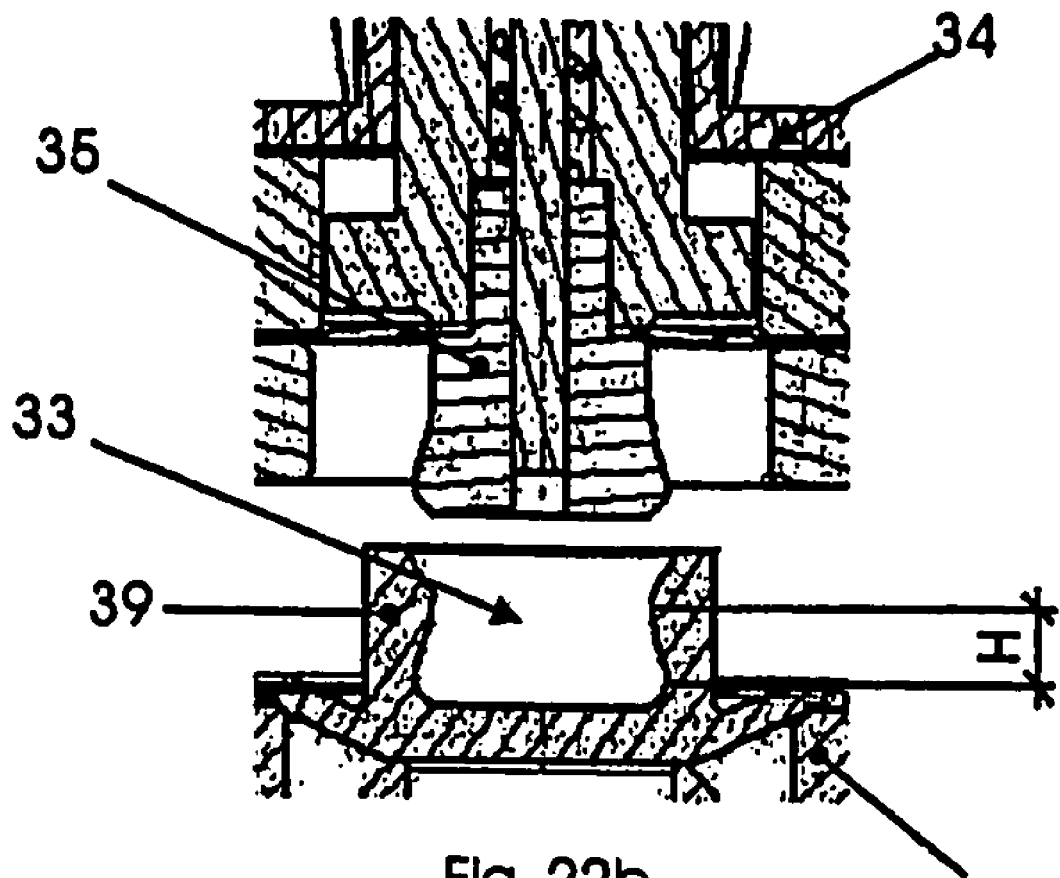
Figure 22B:
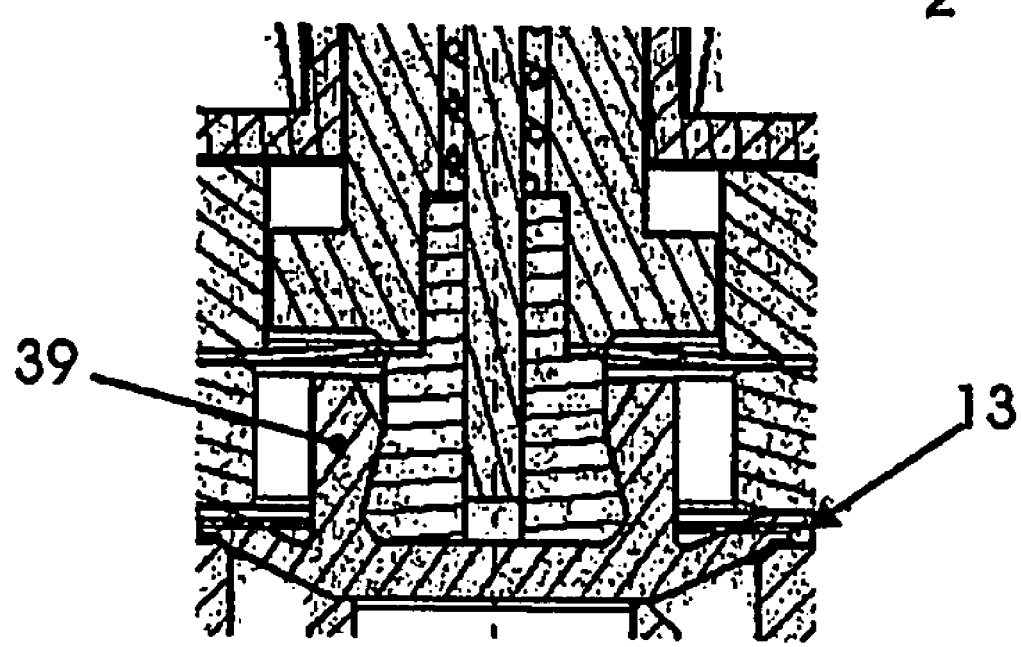
Figure 23:
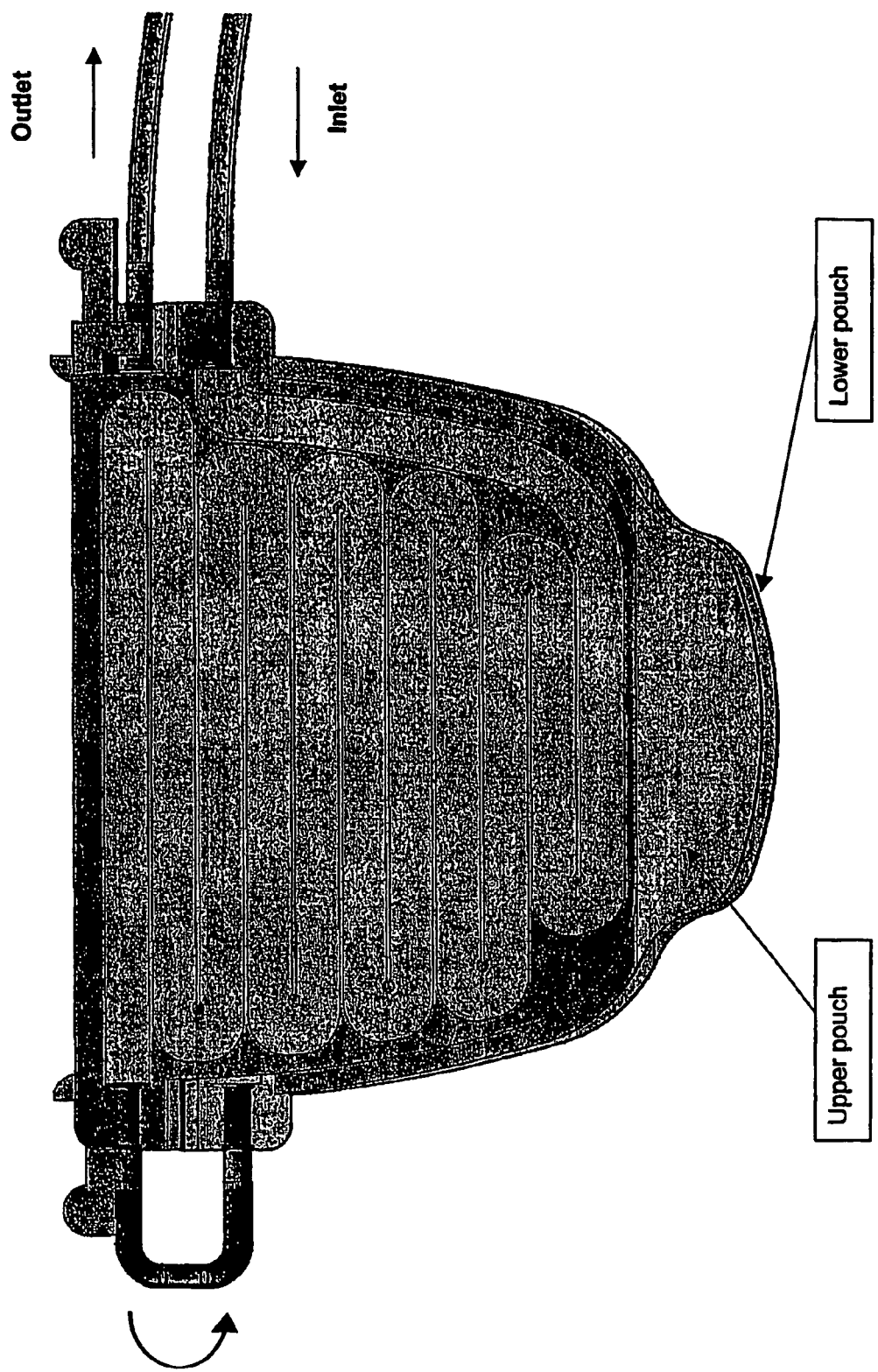
Figure 24A:
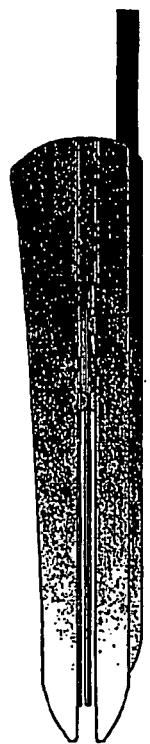
Figure 24B:
Figure 24C:
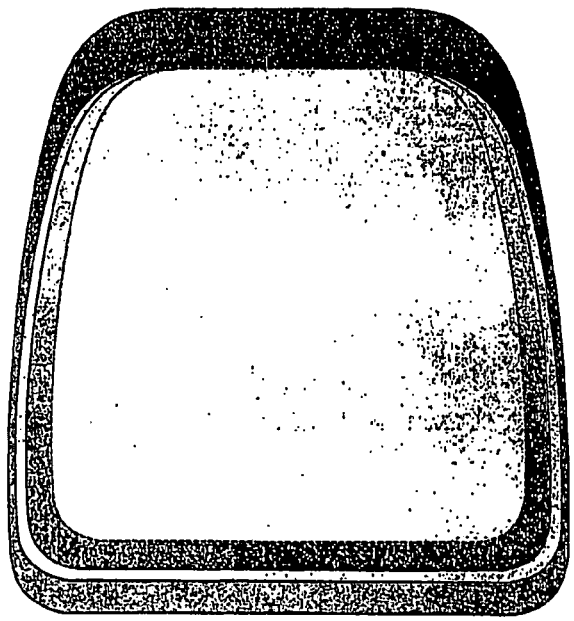

FIG. 1 shows in a schematic way the principle of the invention
FIG. 1A shows the "fill" phase
FIG. 1B shows the "drain" phase
FIG. 2 illustrates a first embodiment of the invention (liquid distribution system)
FIG. 3 illustrates a second embodiment (disposable cartridge) including a warmer chamber
FIG. 4 shows the embodiment of FIG. 3 in a transparent view
FIG. 5 shows the back side of the embodiment of FIG. 3 (disposable cartridge)
FIG. 6 illustrates the disposable cartridge of FIG. 3 with the complete tubing set
FIG. 7 shows an embodiment with the rotative parts (rollers) integrated on the cycler
FIG. 8 shows the embodiment of FIG. 7 without the rollers
FIG. 9 the disposable cartridge in two parts allowing to absorb pump vibrations
FIG. 10 shows a cycler without the cartridge insertion slot
FIG. 11 illustrates a disposable cartridge opened showing the peritoneal pump
FIG. 12 is an upper view of an elastic molded membrane
FIG. 13 is a bottom view of the membrane of FIG. 12
FIG. 14 shows a membrane clipping system
FIG. 15 shows the cycler of FIG. 10 in an open state
FIG. 16 shows a cartridge loader
FIG. 17 shows the cycler of FIG. 10, the insertion slot opened with the cartridge
FIG. 18 shows the cycler of FIG. 10, the insertion slot closed with the cartridge
FIG. 19 shows a front view of a valve
FIG. 20 shows a front view of a pressure sensor
FIG. 21 shows a pump race
FIG. 22 shows a valve actuator and a membrane clipping system
FIG. 23 shows a warmer
FIG. 24 shows a warmer casing
FIG. 25 is a table showing drain profiles

NUMERICAL REFERENCES USED IN THE DRAWINGS

1. Pump
2. Liquid distribution system (cartridge)
3. Supply means (bag)
4. Patient
5. Patient line
6. Drain collector
7. First hub chamber
8. Second hub chamber
9. Liquid supply port with valve
10. Patient port with valve
11. Drain port with valve
12. Roller separator
13. Membrane
14. Membrane frame
15. Pressure sensor cavity (patient)
16. Patient port with valve (warmer chamber)
17. Warmer chamber
18. Patient port with valve (first hub chamber)
19. Warmer port
20. Roller element
21. Pump race
22. Roller
23. Tube connector for warming enter line
24. Liquid supply line
25. Drain line
26. Pump inlet
27. Pump outlet
28. Warmer pouch
29. Warmer enter line
30. Warmer exit line
31. Membrane pressure sensor area
32. Retaining element for pressure sensor
33. Clip cavity
34. Actuator
35. Clip plunger
36. Pressure sensor cavity (first hub chamber)
37. Pump flexible tube
38. Warmer port with valve 39. Membrane actuator clip
40. Membrane pressure volute
41. Cartridge loader
42. Pump motor+coder
43. Air sensor
44. Pressure sensor
45. Pump casing
46. Cartridge loader shaft
47. Cartridge loader frame
48. Cartridge loader linear cam
49. Cartridge loader motor
50. Cartridge insertion slot
51. Cycler
52. Cartridge motor shaft
53. Tube connector for supply line
54. Tube connector for drain line
55. Tube connector for warmer exit line
56. Pump enter line
57. Pump exit line
58. Sensor pressure housing
59. Sealing flange

DETAILED DESCRIPTION OF THE INVENTION

The peritoneal dialysis system according to the invention is shown in a schematic way in FIG. 1. It includes a pump 1, a liquid distribution system 2 (also named cartridge) comprising a first hub chamber 7 and a second hub chamber 8. The first chamber 7 includes a pump inlet 26 connected to the pump 1 via a pump enter line 56, a liquid supply port 9 with valve connected to supply means, e.g. to bags 3, via a liquid supply line 24 and a patient port 10 with valve connected to a patient 4 via a patient line 5. The second chamber 8 includes a pump outlet 27 connected to the pump 1 via a pump exit line 57, a drain port 11 with valve connected to a drain collector 6 via a drain line 25 and a patient port 18 with valve connected to a patient 4 via a patient line 5.

FIG. 1A shows the "fill" phase where liquid is supplied to the patient 4 from and through the following elements: Bag 3—Liquid supply line 24—(open) liquid supply port 9—First chamber 7—Pump inlet 26—Pump enter line 56—Pump 1—Pump exit line 57—Pump outlet 27—Second chamber 8—(open) Patient port 18—Patient line 5—Patient 4.

FIG. 1B shows the "drain" phase where liquid is drained from and through the following elements: Patient 4—Patient line 5—(open) Patient port 10—First chamber 7—Pump inlet 26—Pump enter line 56—Pump 1—Pump exit line 57—Pump outlet 27—Second chamber 8—(open) Drain port 11—Drain line 25—Drain collector 6.

The embodiment illustrated on FIG. 2 shows an assembly constituted by a pumping element 1 and a cartridge 2. Both elements are fixed together but may be separated. FIG. 21 shows a better view of the fixation between both elements. Preferably, the pumping element 1 is fixed to the cartridge 2 by vibration attenuation means in order to minimize the vibration on cartridge 2 when the pump is operating.

The upper face of the cartridge contains a first hub chamber 7, a second distinct hub chamber 8 and a cavity 15 which forms part of a pressure sensor. The first chamber hub chamber 7 has three liquid supply ports 9, one patient port 10, one pump inlet 26 and a cavity 36 which forms part of a pressure sensor. The second hub chamber 8 has a patient port 18, a drain port 11 and a pump outlet 27.

The pumping element 1 comprises a pump casing 45 which contains three rollers 22 maintained around the pump casing center by a roller separator 12. The space between the roller-roller separator element and the pump casing defines a pump race 21 in which a flexible tube 37 is placed. The flexible tube being connected with the pump enter 56 and exit 57 lines. The rollers 22 may be motor driven by a shaft 52 (not shown on FIG. 2) in such a way as to progressively compress the flexible tube 37 resulting thereby in a peristaltic movement along the flexible tube 37.

During the "fill" phase, liquid is supplied via one tube connector 53 and liquid supply port 9 to the first hub chamber 7. It then enters the pump 1 through the pump inlet 26, moves along the flexible tube 37, enters the second hub chamber 8 through the pump outlet 27 and goes to the patient 4 via patient port 18 and patient line 5.

During the "drain" phase, liquid leaves the patient 4, enters the first hub chamber 7 via patient port 10. It then enters the pump 1, moves along the flexible tube 37, enters the second hub chamber 8 and goes to the drain collector 6 via drain port 11, drain tube connector 54 and drain line 25.

It should be noted at this stage that each bag 3 may contain a specific liquid.

The cartridge 2 of FIG. 3 is identical to the cartridge of FIG. 2 with the exception of an additional cavity, namely a warmer chamber 17, which includes a warmer port 19 and a patient port 16. The warmer port 19 is connected to a warmer 28 (not shown on FIG. 3) via a warmer tube connector 55 and a warmer exit line 30. The patient port 16 is connected to the patient line 5. The second hub chamber 8 contains a warmer port 38 connected to a warmer 28 (not shown on FIG. 3) via a warmer tube connector 23 and a warmer enter line 29.

During the "fill" phase, liquid is supplied via one tube connector 53 and liquid supply port 9 to the first hub chamber 7. It then enters the pump 1, moves along the flexible tube 37, enters the second hub chamber 8, moves into the warmer 28 via warmer port 38, enters the warmer chamber 17 via warmer port 19 through the tube connector 55 and goes to the patient 4 via patient port 16 and patient line 5.

As it can be seen on the embodiments of FIGS. 2 and 3, the pump 1 is unidirectional, i.e. whatever the pumping phase is, liquid in the flexible tube 37 always moves in the same direction. This feature provides several advantages. In particular a higher precision in the liquid exchange due to the same flow speed for both the fill and drain phases and a longer life time.

It is known that peristaltic pumps are usually accurate within +/−5%. As such, peristaltic pumps cannot be used for peritoneal dialysis since the volume which is filled within the patient cavity requires to be drained in the same amount within +/−2%, otherwise the peritoneal cavity could be overfilled (e.g. for 12 liters exchanged over the therapy, a 3% difference represents 360 ml which is as much as 18% of the 2 liters contained in the peritoneal cavity for each cycle) and/or the ultra-filtration could be altered. In order to improve on the accuracy of the exchanged volume without requiring the construction of highly accurate pumps which would warranty a +/−2% accuracy, the invention provides a method whereby the conventional pump is used in a unidirectional way which insures the same accuracy for both the fill and the drain phase (usually within +/−2%) and therefore an appropriate balance of fluid. The volume filled with such a pump may be inaccurate within +/−5%, but since the same cassette with the same flow speed characteristics (namely the same flow direction) is used, the balance can be insured within +/−2% as required for the therapy. If the cassette would be used in both directions, the difference in flow speed would be within +/−5% due to the non parallel behavior of peristaltic pumps, in particular over time.

It should be noted that with the present invention, the precision in the liquid exchange is maintained even if the pump flow rate changes after a certain time due to aging of the tubing since the fill and drain are operated within a time window which is small in comparison to the time in which the flow speed is altered by aging (e.g. a flow alteration of the pump of approximately 1% per 20 liters of fluid pumped, with exchanged volumes of approximately 2 liters per cycle). In addition, the use of the cassette in one direction enables a better control over the aging of the tubing and, therefore, a better prediction of the impact on the pumping accuracy.

FIG. 4 is a transparent view of the cartridge which better shows how the different elements are connected. A cartridge bottom view is shown on FIG. 5. The tubing system in the lower face and the cavities of the upper face are all made within one single part, e.g. an injected part of plastic material.

FIG. 6 shows an assembly including the cartridge 2 of FIG. 3 fixed to a pumping element 1, a patient line 5, supply bags 3, a warmer enter line 29, a warmer outer line 30 and a warmer pouch 28 which is essentially made of a fluid circuit within a plastic bag (e.g. PVC) to be put into contact with a warming plate.

FIG. 6" shows a warming plate contained into a warming system where the warming pouch has a shape of a sock to be inserted onto the warming plate. The warming pouch is composed of a liquid channel which forces the liquid to be maintained within such warmer for a certain duration at a given flow rate.

FIG. 7 shows a cartridge identical to the one of FIG. 3 where the rollers are part of the cycler rather than of the cartridge. In this embodiment, the pumping element 1 which only contains the tube and tubing race and the cartridge 2 are forming a single element.

The rollers, which are part of the cycler and therefore re-usable rather than disposable with the cardridge, have a conical shape so as to allow the rollers to be self inserted in the pump race. In this configuration the cartridge is more simple to manufacture and contains less parts. No other insertion mechanism is required, since the tube is automatically compressed on the race while the rollers are penetrating into the cartridge. As a separate matter, the use of conical rollers 22 results in a more constant speed of the liquid along the flexible tube 37.

FIG. 8 shows the assembly of FIG. 7 without the rollers 22 and the roller element.

Of course, other roller shapes may be used, e.g. spherical or cylindrical.

The embodiment of FIG. 9 only differs from the one of FIG. 8 in that the pump casing 45 is made out of two parts with an interface between the pumping element 1 and the cartridge 2. This configuration offers an improved assembly process of the pump and the possibility to add means to limit the propagation of the vibrations from the pump 1 to the cartridge 2.

FIG. 10 shows a cycler 51 without cartridge 2 and pumping element 1. It contains a driving zone which includes a motor shaft 52 for the rollers 22 and several actuators 34. The cycler 51 also includes an air sensor 43 situated close to the patient line 5 when the cartridge 2 is inserted. The air sensor may be made of a piezo emitter and a piezo receiver.

FIG. 11 represents the embodiment of FIG. 2 with a flexible membrane 13 covering the hub chambers 7,8 and the pressure sensor cavity 15.

The upper face of the membrane 13 (see FIG. 12) contains several valve elements having a cylindrical cavity 39 and a pressure sensor area 31 with a ply 40 around its periphery. The valve elements 39 are designed to tightly close the ports when the membrane 13 moves downwardly.

On its bottom face (see FIG. 13) the membrane 13 contains a semi-circular flange 32 around the pressure sensor area and annular liquid tight joints.

In addition the cartridge 2 includes liquid tight joints arranged in such a manner that they allow a liquid tight connection between the cartridge 2 and the membrane 13.

Advantageously the membrane is molded. Preferably the membrane 13 is made of silicone.

The membrane 13 is press-fitted to the cartridge 2 along its periphery with a membrane frame 14 (see FIG. 14).

FIG. 15 shows the cycler of FIG. 10 in an open state which includes a pump motor and a coder 42. The rectangle 41 represents the cartridge loader.

FIG. 16 shows a cartridge loader comprising cartridge loader shafts 46, a cartridge loader frame 47, a cartridge loader linear cam 48 and a cartridge loader motor 49. On this figure, the two displacement parts 48' and 48" represent two different positions of the loader in an open and closed position only for explanation reasons.

The cartridge loading mechanism allows a tight connection between the membrane and the valves and the cartridge. In order to insure proper positioning of the cartridge onto the valve actuators, as well as pressure sensor and air sensor onto the right place, the cartridge is maintained into the loading mechanism which progressively moves the cartridge in an axis which is perpendicular to its surface. By the same movement, the axis or the rollers can be inserted in the right position to ensure proper functioning of the pump. The same movement can also insure appropriate pressure on the surfaces which requires to be maintained together, such as for tightness control on the membrane and/or tubing of the pump.

FIG. 17 shows the cycler 51 of FIG. 10 containing a cartridge 2. The cycler 51 has an insertion slot 50 in an open position.

FIG. 18 shows the same cycler 51 but with an insertion slot in a closed position.

FIG. 19 represents an actuator 34 with its plunger 35 clipped in its corresponding valve element 39 of the membrane. The actuator 34 may be a magnet or an electromagnetic element. The plunger 35 and the valve element 39 are designed to move together when the actuator is activated.

FIG. 22a and 22b shows the plunger 35 and the valve element 39 in a separate position (FIG. 22a) before insertion and in an activated position (FIG. 22b) after insertion. One embodiment of the invention is to insure a proper insertion of the actuator head into the membrane clipping part by having the length of the part of the actuator head to be inserted into the clip of the membrane to be longer than the possible displacement of the actuator head, so as to ensure that the actuator head is always properly inserted into the clip of the membrane. As such, in the worst case where the actuator head would be fully retracted within the actuator during the clipping translation into the membrane, the actuator head would pass the clipping equilibrium position before the end of the translation, so that the remaining translation will ensure clipping of the actuator head into the membrane.

The front view of FIG. 20 illustrates a pressure sensor 44 which may be used with the independent pressure sensor cavity 15 of the cartridge 2 or with the pressure sensor cavity 36 of the first hub chamber 7. The ply 40 makes the pressure sensor less sensitive to the elasticity of the membrane 13 in the sensor pressure area. In addition, the shape of the cavity 15 shall be made such that air can be eliminated easily when fluid is passing into the cavity (e.g. by having a round shaped bottom of the cavity within the direction of the flow).

In the embodiments discussed previously, each port has a dedicated valve. This is not the case for the pump inlet and the pump outlet which are always kept open.

The invention encompasses several other features not necessarily illustrated on the figures. For instance, the cycler or the cartridge-pumping element assembly may contain a window for detecting correct positioning of the flexible tube of the pump as shown in FIG. 21 (circle).

When the system functions, the pressure is preferably always maintained positive with respect to the drain. This is a safety measure which avoids said contaminated liquid to potentially infect the patient.

Advantageously the liquid pressure entering and exiting the cartridge is sensed and, if necessary, the pump flow rate is corrected in accordance with the pressure difference. This pressure difference is better calculated at the initial priming phase of the system, where the pressure is directly related to the positioning of the liquid bags 3 and the patient position relative to the cycler.

Alternatively or in addition, the pump flow rate may be regulated according to a predetermined deterioration of the tubing which is known from the characteristics of the tubing.

The drain phase may be limited as to its duration in function of the drain speed, the drain speed having to be reduced when the patient peritoneal cavity pressure decreases, typically between 30 ml/min and 120 ml/min instead of a nominal 200 ml/min speed. This feature is particularly interesting because the dialysis efficiency is directly related to the time the liquid stays in the peritoneal cavity and the duration required to fully drain the peritoneal cavity may limit this time without a significant impact with regard to the peritoneal fluid characteristics. As such, one method of the invention would be to determine at which speed it is not worth continuing draining the patient entirely and rather fill the patient with fresh fluid, taking into consideration the remaining fluid volume in the peritoneal cavity which has not been expelled and expected ultra-filtration additional volume to avoid overfill. The cycles will therefore be all different, based on reaching a pre-determined drainage speed or a pre-determined decrease profile of the drainage speed, so that the efficient time of dialysis will be increased. An example of drainage speed on a patient is given in the FIG. 25, where, for each column which is divided in three parts, the upper part corresponding to a limit of drainage speed at which it is, for example, not worth continuing the drainage even if the next fill volume will not be a full fill. In comparison to actual method where a tidal at (e.g. 80%) is preset, the method under the invention is adapting each drainage to the actual drainage speed, trying to empty as much as possible without compromising on the efficacy of the peritoneal dialysis. Of course some limits can be set, where a minimum of drainage volume has to be reached before such a limitation takes place for each cycle.

Another method under the present invention consists to fill always as much volume, within certain limits to be set for the patient, until a certain pressure in the peritoneal cavity is reached. As such, the peritoneal dialysis can be improved since the efficiency is related to the amount of fluid filled at every cycle. According to such method, the pump shall fill the patient until a certain pressure is reached (e.g. 10 cm water) and stop only once such pressure is reached or a certain maximum volume is reached. Accordingly, it is important to measure continuously the pressure during the dwell time to make sure that no over pressure is reached, such as due to the ultra-filtration. One possibility is also to always fill up to such a limited pressure and/or volume and drain at a certain interval thereafter a certain volume to compensate for expected ultra-filtration. Another possibility is to increase the ultra-filtration during the last cycle, by using e.g. low sodium concentrated solution.

The invention claimed is:

1. A system for performing fluid administration on a patient comprising:
    a single liquid pump,
    a liquid distribution system connected to said pump in such a way that liquid can flow from the liquid distribution system to the pump via a pump enter line and vice versa via a pump exit line,
    liquid supply means for supplying liquid to a patient via said liquid distribution system and said pump,
    a patient conduit adapted for connecting said liquid distribution system to a patient,
    a drain collector,
    wherein said liquid pump is unidirectional and said liquid distribution system comprises switching means comprising valves designed to alternatively connect the pump enter line with the supply means or with the patient conduit, said system further comprising two distinct lines, namely:
    a first line including successively said liquid supply means, said liquid distribution system, said liquid pump, said liquid distribution system and said patient conduit, and
    a second line including successively said patient conduit, said liquid distribution system, said liquid pump, said liquid distribution system and said drain collector.

2. A system according to claim 1 wherein the liquid pump is a peristaltic pump.

3. A system according to claim 2 wherein the peristaltic pump is rotatable.

4. A system according to claim 1 wherein said liquid distribution system comprises two distinct hub chambers, the first hub chamber including at least one liquid supply port with dedicated valve means, one patient port with dedicated valve means and one pump inlet, the second hub chamber including at least, one patient port or warmer port with dedicated valve means and one pump outlet, said system further comprising control means arranged to close said patient port of the first hub chamber when said liquid supply port is open and vice versa.

5. A system according to claim 4 wherein said second hub chamber further includes at least one drain port with dedicated valve means, said control means being also arranged to close said patient port of the second hub chamber when said drain port is open and vice versa.

6. A system according to claim 5 wherein said liquid distribution system only includes two hub chambers.

7. A system according to claim 1 further comprising a warmer system, a cavity including a warmer port and a patient port, said patient port of the second hub chamber being connected to said warmer port via said warmer system.

8. A system according to claim 4 wherein said first hub chamber includes several liquid supply ports with respective valve means.

9. A system according to claim 8 wherein said liquid supply ports are connected to respective liquid supply means having each a different kind of liquid.

10. A system according to claim 1 wherein said liquid pump is composed of a tubing and rolling surface on which the tubing is compressed once the cartridge is inserted into a pumping device containing rollers.

11. A system according to claim 1 wherein said liquid pump and said liquid distribution system are fixed together to form a single cartridge.

12. A system according to claim 11 wherein said liquid pump is fixed to said liquid distribution system by vibration attenuation means in order to minimize the vibration on the liquid distribution system when the pump is operating.

13. A system according to claim 1 wherein all hub chambers, including ports, are made within one single part.

14. A system according to claim 13 wherein said single part is an injected part of plastic material.

15. A system according to claim 1 wherein each hub chamber is closed with an upper wall made of a flexible membrane, said membrane including valve elements situated above each of said port or port with valve means, said valve elements being designed to close said port or port when the membrane moves downwardly.

16. A system according to claim 1 wherein said liquid distribution system includes liquid tight joints arranged in such a manner that they allow a liquid tight connection between said liquid distribution system and a membrane situated on it.

17. A system according to claim 1 wherein said liquid distribution system includes an air sensor situated on the patient conduit side.

18. A system according to claim 1 comprising a cartridge loading mechanism which allows a tight connection between the membrane and the valves and the liquid distribution system.

19. A liquid distribution system for a system performing fluid administration on a patient as defined in any one of the previous claims.

20. A pressure sensor for a system for performing fluid administration on a patient as defined in claim 1.

21. A system according to claim 1 further comprising a window for detecting correct positioning of a pump flexible tube.

* * * * *